(12) United States Patent
Tiron et al.

(10) Patent No.: US 12,721,567 B2
(45) Date of Patent: Sep. 1, 2026

(54) SYSTEMS AND METHODS FOR DETECTING REM BEHAVIOR DISORDER

(71) Applicant: ResMed Sensor Technologies Limited, Dublin (IE)

(72) Inventors: Roxana Tiron, Dublin (IE); Ehsan Chah, Dublin (IE); Hannah Meriel Kilroy, Dublin (IE); Marta Perez Denia, Dublin (IE); Kieran Conway, Dublin (IE)

(73) Assignee: ResMed Sensor Technologies Limited, Dublin (IE)

( * ) Notice: Subject to any disclaimer, the term of this patent is extended or adjusted under 35 U.S.C. 154(b) by 669 days.

(21) Appl. No.: 17/915,779

(22) PCT Filed: Mar. 31, 2021

(86) PCT No.: PCT/IB2021/052669
§ 371 (c)(1),
(2) Date: Sep. 29, 2022

(87) PCT Pub. No.: WO2021/198934
PCT Pub. Date: Oct. 7, 2021

(65) Prior Publication Data

US 2023/0240595 A1 Aug. 3, 2023

Related U.S. Application Data

(60) Provisional application No. 63/003,240, filed on Mar. 31, 2020.

(51) Int. Cl.
*A61B 5/00* (2006.01)
*A61B 5/08* (2006.01)
(Continued)

(52) U.S. Cl.
CPC .......... *A61B 5/4812* (2013.01); *A61B 5/0816* (2013.01); *A61B 5/1114* (2013.01);
(Continued)

(58) Field of Classification Search
CPC ... A61B 5/4812; A61B 5/0816; A61B 5/1114; A61B 5/4803; A61B 5/4815;
(Continued)

(56) References Cited

U.S. PATENT DOCUMENTS 10,964,195 B1 * 3/2021 Huang .................... G08B 3/10
11,147,505 B1 * 10/2021 Shoeb ................. A61B 5/6801
(Continued)

FOREIGN PATENT DOCUMENTS

CN 104812300 A 7/2015
CN 106510663 A 3/2017
(Continued)

OTHER PUBLICATIONS

Howelll et al., "A Novel Therapy for REM Sleep Behavior Disorder (RBD)", Journal of Clinical Sleep Medicine, 2011, vol. 7, No. 6, 639-644A.
(Continued)

*Primary Examiner* — Niketa Patel
*Assistant Examiner* — Attiya Sayyada Hussaini
(74) *Attorney, Agent, or Firm* — Nixon Peabody LLP

(57) ABSTRACT

A method for monitoring a sleep session of an individual comprises receiving data associated with a current sleep session of the individual; analyzing at least a portion of the received data to identify one or more sleep stages experienced by the individual during the current sleep session, the one or more sleep stages including a light sleep stage, a deep sleep stage, a typical rapid eye movement (REM) stage, an atypical REM stage, a wake stage, or any combination thereof; and generating a summary of the current sleep
(Continued)

session, the summary including (i) a number of atypical REM sleep stages experienced by the individual during the sleep current sleep session, (ii) a time spent in atypical REM sleep stages during the current sleep session, or (iii) both (i) and (ii).

20 Claims, 11 Drawing Sheets

(51) Int. Cl.
*A61B 5/11* (2006.01)
*G16H 10/60* (2018.01)
*G16H 40/67* (2018.01)

(52) U.S. Cl.
CPC .......... *A61B 5/4803* (2013.01); *A61B 5/4815* (2013.01); *A61B 5/7246* (2013.01); *A61B 5/7267* (2013.01); *G16H 10/60* (2018.01); *G16H 40/67* (2018.01)

(58) Field of Classification Search
CPC ....... A61B 5/7246; A61B 5/7267; A61B 5/11; A61B 5/4836; G16H 10/60; G16H 40/67
See application file for complete search history.

(56) References Cited

U.S. PATENT DOCUMENTS 11,883,188 B1 * 1/2024 Kahn ....................... A61B 5/11
12,016,698 B2 * 6/2024 Garcia Molina ...... G16H 20/70
2008/0262373 A1 10/2008 Burns et al.
2011/0160603 A1 6/2011 Langston et al.
2012/0053508 A1 3/2012 Wu et al.
2014/0088373 A1 * 3/2014 Phillips .................... A61B 5/05 600/301
2015/0119741 A1 * 4/2015 Zigel ...................... A61B 7/003 600/529
2015/0126821 A1 5/2015 Kempfner et al.
2017/0086732 A1 3/2017 Tribble et al.
2017/0273617 A1 * 9/2017 Kaji ..................... A61B 5/6892
2018/0242902 A1 * 8/2018 Martinmäki .......... A61B 5/1118
2019/0069839 A1 3/2019 Park et al.
2019/0223781 A1 * 7/2019 Arrington ............ A61B 5/7455
2020/0397365 A1 * 12/2020 Zhang .................... G16H 50/20
2023/0148956 A1 * 5/2023 Narayanan ........... A61B 5/4809 600/301

FOREIGN PATENT DOCUMENTS

CN 106691686 A 5/2017
CN 107875496 A 4/2018
CN 110366387 A 10/2019
CN 110558946 A 12/2019
EP 0773504 A1 * 5/1997
JP 2016-22310 A 2/2016
JP 2019195469 A 11/2019
JP 2020-22732 B1 2/2020
WO 2014/047310 A1 3/2014
WO 2016/061629 A1 4/2016
WO 2017/132726 A1 8/2017
WO 2018/050913 A1 3/2018
WO 2019/122413 A1 6/2019
WO 2019/122414 A1 6/2019
WO 2019/212901 A1 11/2019
WO 2020/104465 A2 5/2020

OTHER PUBLICATIONS

International Search Report in International Patent Application No. PCT/IB2021/052669 mailed Jul. 2, 2021 (6 pp.).
Written Opinion in International Patent Application No. PCT/IB2021/052669 mailed Jul. 2, 2021 (8 pp.).
Cooray N. et al., "Detection of REM sleep behaviour disorder by automated polysomnography analysis", Clinical Neurophysiology, vol. 130, No. 4; Feb. 6, 2019 (Feb. 6, 2019), pp. 505-514.

* cited by examiner

Figure 7A:
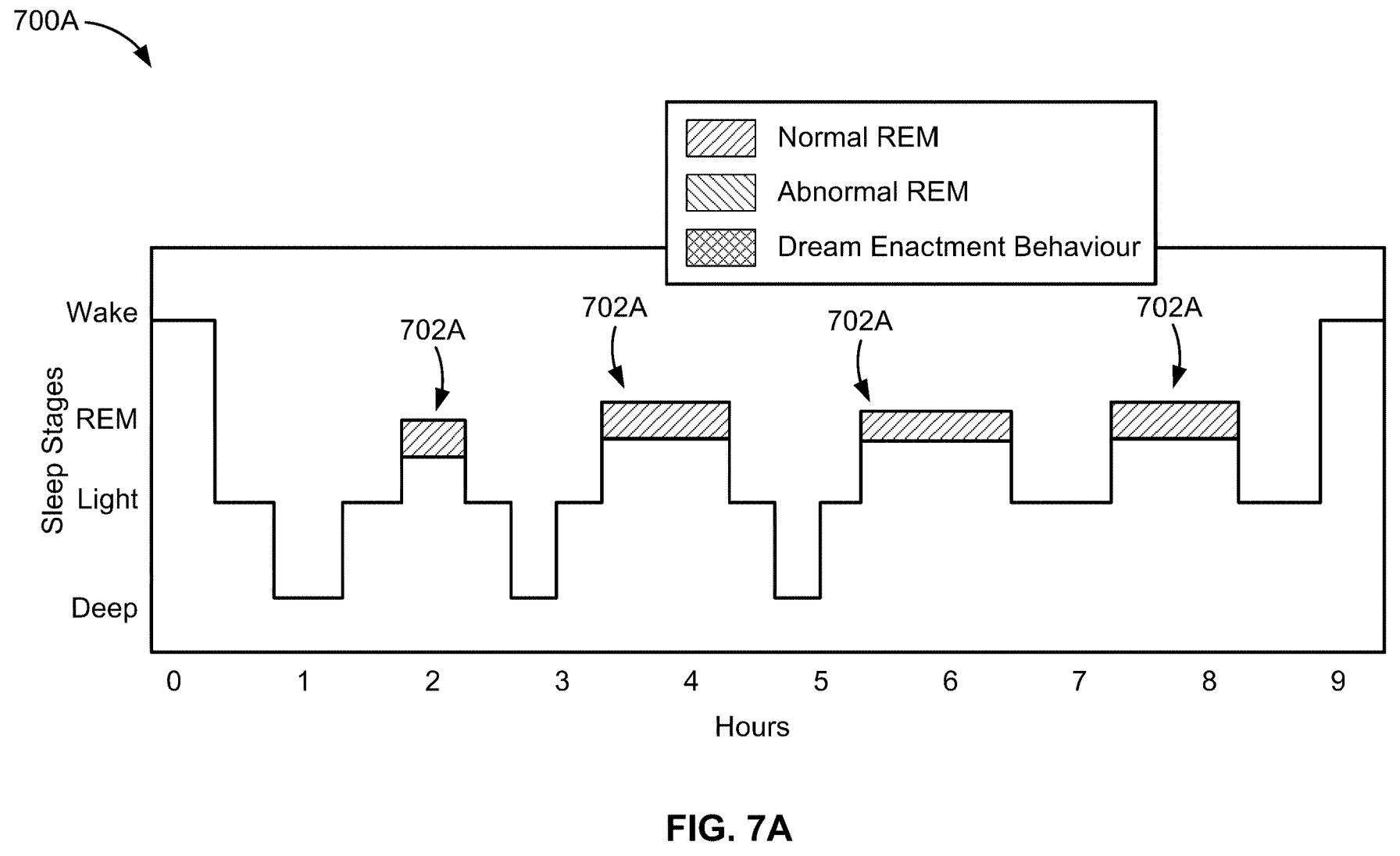

700A

Sleep Stages

Wake

REM

Light

Deep

Hours 0 1 2 3 4 5 6 7 8 9

Normal REM

Abnormal REM

Dream Enactment Behaviour

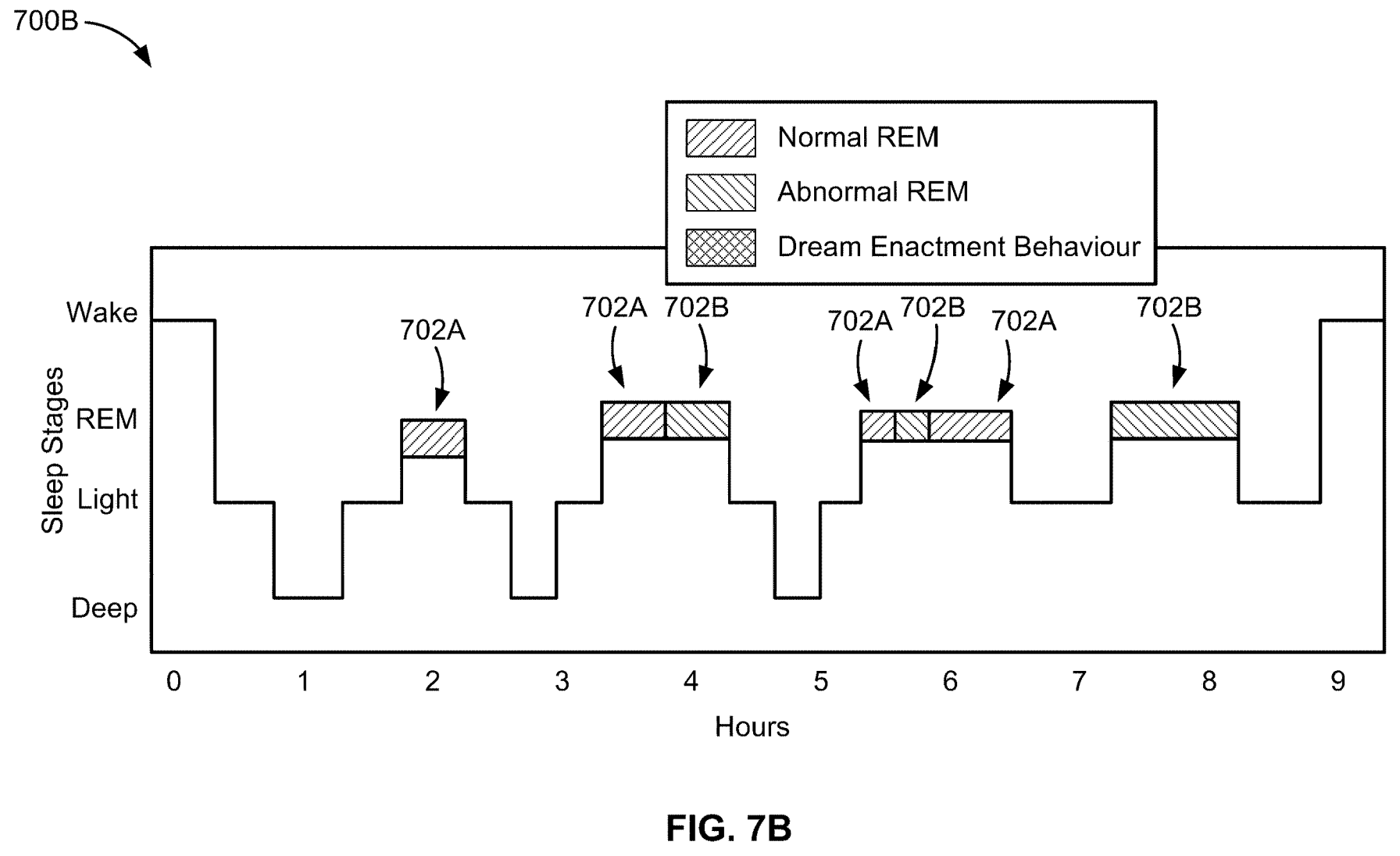

Normal REM
Abnormal REM
Dream Enactment Behaviour 702A
702A
702B
702A
702B
702A
702B Sleep Stages
Wake
REM
Light
Deep 0 1 2 3 4 5 6 7 8 9
Hours

FIG. 7B

SYSTEMS AND METHODS FOR DETECTING REM BEHAVIOR DISORDER

CROSS-REFERENCE TO RELATED APPLICATIONS

This application is a U.S. National Stage of International Application No. PCT/IB2021/052669, filed on Mar. 31, 2021, which claims the benefit of, and priority to, U.S. Provisional Patent Application No. 63/003,240, filed on Mar. 31, 2020, each of which is hereby incorporated by reference herein in its entirety.

TECHNICAL FIELD

The present disclosure relates generally to systems and methods for detecting rapid eye movement (REM) behavior disorder, and more particularly, to systems and methods for long-term monitoring of REM behavior disorder and real-time mitigation of dream enactment behavior.

BACKGROUND

Many individuals suffer from sleep-related disorders and/or respiratory-related, such as insomnia (e.g., difficulty initiating sleep, frequent or prolonged awakenings after initially falling asleep, and an early awakening with an inability to return to sleep), periodic limb movement disorder (PLMD), Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD), etc. One such sleep-related disorder is rapid eye movement behavior disorder, also known as REM behavior disorder or RBD. RBD is characterized by a lack of muscle atonia during REM sleep, and in more severe cases movement and speech produced by an individual during REM sleep stages. RBD can sometimes be accompanied by dream enactment behavior (DEB), where the individual acts out dreams they may be having, sometimes resulting in injuries to themselves or their partners. RBD is often a precursor to a subclass of neuro-degenerative disorders, such as Parkinson's disease, Lewis Body Dementia, and Multiple System Atrophy. Typically, RBD is diagnosed in a sleep laboratory via polysomnography. This process can be expensive, and often occurs late in the evolution process of the disease, when mitigating therapies are difficult to adopt and/or less effective. It can be difficult to monitor an individual during sleep and accurately determine whether the individual is suffering from RBD or DEB. Thus, it would be advantageous to be able to accurately detect and mitigate RBD and DEB. The present disclosure is directed to systems and methods for non-invasive screening of RBD that can be used long-term with little hindrance to the subject, facilitating early detection of RBD and associated neuro-degenerative disorders.

SUMMARY

According to some implementations of the present disclosure, a method for monitoring a sleep session of an individual method comprises receiving data associated with a current sleep session of the individual; analyzing at least a portion of the received data to identify one or more sleep stages experienced by the individual during the current sleep session, the one or more sleep stages including a light sleep stage, a deep sleep stage, a typical rapid eye movement (REM) stage, an atypical REM stage, a wake stage, or any combination thereof; and generating a summary of the current sleep session, the summary including (i) a number of atypical REM sleep stages experienced by the individual during the sleep current sleep session, (ii) a time spent in atypical REM sleep stages during the current sleep session, or (iii) both (i) and (ii).

According to some implementations of the present disclosure, a method for monitoring a sleep session of an individual method comprises receiving data associated with a sleep session of an individual; identifying, using one or more trained algorithms, one or more sleep stages experienced by the individual during the sleep session, the one or more sleep stages of the individual including a light sleep stage, a deep sleep stage, a typical rapid eye movement (REM) sleep stage, an atypical REM sleep stage, a wake state, or any combination thereof; determining a total number of atypical REM sleep stages experienced by the individual during the sleep session; determining a total amount of time the individual experienced the atypical REM sleep stages during the sleep session; and in response to (i) the total number of atypical REM sleep stages satisfying a first threshold, causing an action to be performed, (ii) the total amount of time satisfying a second threshold, causing the action to be performed, or (iii) both (i) and (ii).

According to some implementations of the present disclosure, a method for monitoring a sleep session of an individual method comprises determining, based at least in part on historical physiological data associated with a plurality of prior sleep sessions of an individual, a value of a historical sleep parameter that is associated with a severity of atypical rapid eye movement (REM) sleep stages experienced by the individual during the plurality of prior sleep sessions; receiving current physiological data associated with a current sleep session of the individual; determining, during the current sleep session, a value of a current sleep parameter that is associated with a severity of one or more atypical REM sleep stages experienced by the individual during the current sleep session; comparing the value of the historical parameter to the value of the current parameter; and in response to the comparison indicating that the severity of at least one of the one or more atypical REM sleep stages experienced by the individual during the current sleep session is greater than a historical severity of atypical REM sleep stages experienced by the individual, causing an action to be performed.

According to some implementations of the present disclosure, a method for monitoring a sleep session of an individual method comprises receiving data associated with a current sleep session of an individual, the received data including (i) respiration data, (ii) motion data indicative of motion of the individual during the current sleep session, (iii) audio data indicative of sound detected during the current sleep session, (iv) optical data indicative of light in an area where the individual is located during the sleep session, or (v) any combination thereof; inputting at least a portion of the received data into a trained dream enactment behavior (DEB) algorithm to determine if the individual is experiencing DEB during the current sleep session; and in response to determining that the individual is experiencing DEB, causing an action to be performed to (i) aid in ending the DEB, (ii) aid in mitigating an impact of the DEB on the individual, (iii) aid in mitigating an impact of the DEB on a bed partner of the individual, or (iv) any combination thereof.

The above summary is not intended to represent each implementation or every aspect of the present disclosure.

Additional features and benefits of the present disclosure are apparent from the detailed description and figures set forth below.

BRIEF DESCRIPTION OF THE DRAWINGS

FIG. 7A is a hypnogram of a user experiencing only typical rapid eye movement sleep stages during a sleep session, according to some implementations of the present disclosure;

FIG. 7B is a hypnogram of a user experiencing typical rapid eye movement sleep stages and atypical rapid eye movement sleep stages behavior during a sleep session, according to some implementations of the present disclosure;

Figure 1:
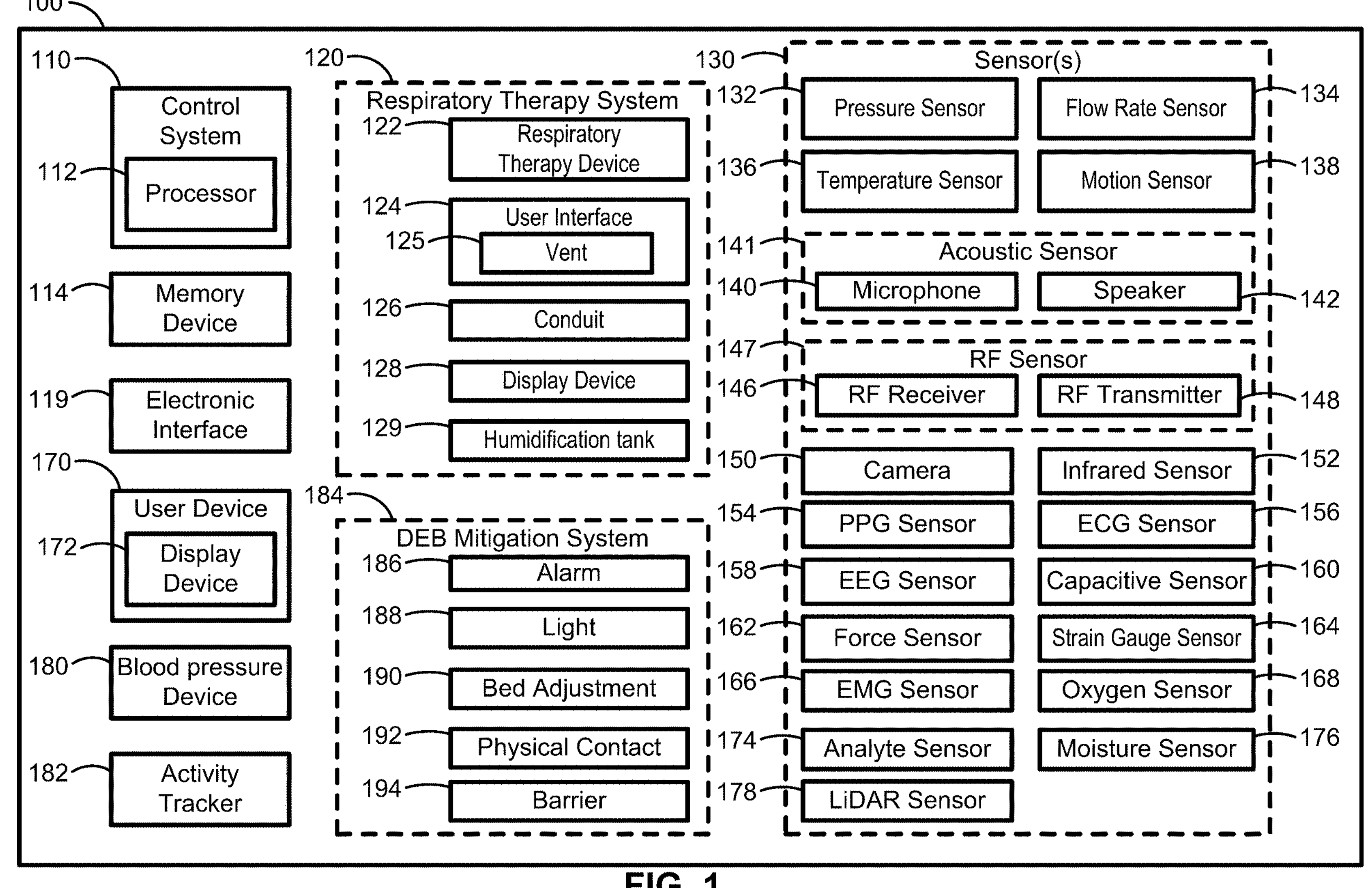
FIG. 1 is a functional block diagram of a system for monitoring a sleep session, according to some implementations of the present disclosure.

While the present disclosure is susceptible to various modifications and alternative forms, specific implementations and embodiments thereof have been shown by way of example in the drawings and will herein be described in detail. It should be understood, however, that it is not intended to limit the present disclosure to the particular forms disclosed, but on the contrary, the present disclosure is to cover all modifications, equivalents, and alternatives falling within the spirit and scope of the present disclosure as defined by the appended claims.

DETAILED DESCRIPTION

Many individuals suffer from sleep-related and/or respiratory-related disorders. Examples of sleep-related and/or respiratory-related disorders include Periodic Limb Movement Disorder (PLMD), Restless Leg Syndrome (RLS), Sleep-Disordered Breathing (SDB), Obstructive Sleep Apnea (OSA), Central Sleep Apnea (CSA), other types of apneas, Cheyne-Stokes Respiration (CSR), respiratory insufficiency, Obesity Hyperventilation Syndrome (OHS), Chronic Obstructive Pulmonary Disease (COPD), Neuromuscular Disease (NMD), chest wall disorders, and rapid eye movement (REM) behavior disorder, also referred to as RBD.

Obstructive Sleep Apnea (OSA) is a form of Sleep Disordered Breathing (SDB), and is characterized by events including occlusion or obstruction of the upper air passage during sleep resulting from a combination of an abnormally small upper airway and the normal loss of muscle tone in the region of the tongue, soft palate and posterior oropharyngeal wall.

Central Sleep Apnea (CSA) is another form of SDB that results when the brain temporarily stops sending signals to the muscles that control breathing. More generally, an apnea generally refers to the cessation of breathing caused by blockage of the air or the stopping of the breathing function. Typically, the individual will stop breathing for between about 15 seconds and about 30 seconds during an obstructive sleep apnea event. Mixed sleep apnea is another form of SDB that is a combination of OSA and CSA.

Other types of apneas include hypopnea, hyperpnea, and hypercapnia. Hypopnea is generally characterized by slow or shallow breathing caused by a narrowed airway, as opposed to a blocked airway. Hyperpnea is generally characterized by an increase depth and/or rate of breathing. Hypercapnia is generally characterized by elevated or excessive carbon dioxide in the bloodstream, typically caused by inadequate respiration.

Cheyne-Stokes Respiration (CSR) is another form of SDB. CSR is a disorder of a patient's respiratory controller in which there are rhythmic alternating periods of waxing and waning ventilation known as CSR cycles. CSR is characterized by repetitive de-oxygenation and re-oxygenation of the arterial blood.

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common, such as increased resistance to air movement, extended expiratory phase of respiration, and loss of the normal elasticity of the lung.

Neuromuscular Disease (NMD) encompasses many diseases and ailments that impair the functioning of the muscles either directly via intrinsic muscle pathology, or indirectly via nerve pathology. Chest wall disorders are a group of thoracic deformities that result in inefficient coupling between the respiratory muscles and the thoracic cage.

These and other disorders are characterized by particular events (e.g., snoring, an apnea, a hypopnea, a restless leg, a sleeping disorder, choking, an increased heart rate, labored breathing, an asthma attack, an epileptic episode, a seizure, or any combination thereof) that occur when the individual is sleeping.

The Apnea-Hypopnea Index (AHI) is an index used to indicate the severity of sleep apnea during a sleep session. The AHI is calculated by dividing the number of apnea and/or hypopnea events experienced by the user during the sleep session by the total number of hours of sleep in the sleep session. The event can be, for example, a pause in breathing that lasts for at least 10 seconds. An AHI that is less than 5 is considered normal. An AHI that is greater than or equal to 5, but less than 15 is considered indicative of mild sleep apnea. An AHI that is greater than or equal to 15, but less than 30 is considered indicative of moderate sleep apnea. An AHI that is greater than or equal to 30 is considered indicative of severe sleep apnea. In children, an AHI that is greater than 1 is considered abnormal. Sleep apnea can be considered "controlled" when the AHI is normal, or when the AHI is normal or mild. The AHI can also be used in combination with oxygen desaturation levels to indicate the severity of Obstructive Sleep Apnea.

RBD is a disorder characterized by movement patterns and vocalizations during REM sleep. When an individual is sleeping, the individual undergoes various different sleep stages, which can include a light sleep stage (stages N1 and N2), a deep sleep stage (stage N3), and a REM sleep stage. Generally, REM sleep stages are characterized by rapid eye movement, as well as muscle atonia, e.g., muscle paralysis. However, individuals suffering from RBD often exhibit a lack of muscle atonia, and undergo various movement patterns during REM sleep stages. These movement patterns can include primitive movements such as jerky movements of the head, neck, trunk, arms, legs, hands, feet, etc. The movement patterns can also be more complex and purposeful movements, such as gesturing, pointing, punching, kicking, etc.

Individuals suffering from RBD may also exhibit various types of vocalizations during atypical REM sleep stages, such as speech (e.g., sleep-talking), muttering (comprehensible or incomprehensible), crying, or other types of non-speech. Furthermore, those suffering from RBD can progress to exhibiting dream enactment behavior (DEB) during atypical REM sleep stages. When an individual experiences DEB, the movement and vocalizations take the form of acting out any dreams the individual may be having. As used herein, RBD is a sleep-related disorder characterized by atypical REM sleep stages. When a person with RBD experiences an atypical REM sleep stage, the person often exhibits more movement and vocalizations than those without RBD. In some instances, the atypical REM sleep stages of those suffering from RBD also include DEB. However, not all atypical REM sleep stages are characterized by DEB, and not all those suffering from RBD experience DEB.

Referring to FIG. 1, a system 100, according to some implementations of the present disclosure, is illustrated. The system 100 is for monitoring a user during a sleep session, in order to determine whether the user is experiencing RBD. Generally, the system 100 is configured to determine when the user is experiencing REM sleep stages that differ from typical REM sleep stages, e.g., are characterized by movement and/or vocalizations. These REM sleep stages that occur in a user suffering from RBD are referred to as atypical REM sleep stages. The system 100 includes a control system 110, a memory device 114, an electronic interface 119, one or more sensors 130, one or more external devices 170, and a DEB mitigation system 184. In some implementations, the system 100 further includes a respiratory therapy system 120 (that includes a respiratory therapy device 122), a blood pressure device 180, an activity tracker 182, or any combination thereof.

The control system 110 includes one or more processors 112 (hereinafter, processor 112). The control system 110 is generally used to control (e.g., actuate) the various components of the system 100 and/or analyze data obtained and/or generated by the components of the system 100. The processor 112 can be a general or special purpose processor or microprocessor. While one processor 112 is shown in FIG. 1, the control system 110 can include any suitable number of processors (e.g., one processor, two processors, five processors, ten processors, etc.) that can be in a single housing, or located remotely from each other. The control system 110 (or any other control system) or a portion of the control system 110 such as the processor 112 (or any other processor(s) or portion(s) of any other control system), can be used to carry out one or more steps of any of the methods described and/or claimed herein. The control system 110 can be coupled to and/or positioned within, for example, a housing of the external device 170, and/or within a housing of one or more of the sensors 130. The control system 110 can be centralized (within one such housing) or decentralized (within two or more of such housings, which are physically distinct). In such implementations including two or more housings containing the control system 110, such housings can be located proximately and/or remotely from each other.

The memory device 114 stores machine-readable instructions that are executable by the processor 112 of the control system 110. The memory device 114 can be any suitable computer readable storage device or media, such as, for example, a random or serial access memory device, a hard drive, a solid state drive, a flash memory device, etc. While one memory device 114 is shown in FIG. 1, the system 100 can include any suitable number of memory devices 114 (e.g., one memory device, two memory devices, five memory devices, ten memory devices, etc.). The memory device 114 can be coupled to and/or positioned within a housing of the respiratory therapy device 122 of the respiratory therapy system 120, within a housing of the external device 170, within a housing of one or more of the sensors 130, or any combination thereof. Like the control system 110, the memory device 114 can be centralized (within one such housing) or decentralized (within two or more of such housings, which are physically distinct).

In some implementations, the memory device 114 (FIG. 1) stores a user profile associated with the user. The user profile can include, for example, demographic information associated with the user, biometric information associated with the user, medical information associated with the user, self-reported user feedback, sleep parameters associated with the user (e.g., sleep-related parameters recorded from one or more earlier sleep sessions), or any combination thereof. The demographic information can include, for example, information indicative of an age of the user, a gender of the user, a race of the user, a family medical history (such as a family history of insomnia or sleep apnea), an employment status of the user, an educational status of the user, a socioeconomic status of the user, or any combination thereof. The medical information can include, for example, information indicative of one or more medical conditions associated with the user, medication usage by the user, or both. The medical information data can further include a multiple sleep latency test (MSLT) result or score and/or a Pittsburgh Sleep Quality Index (PSQI) score or value. The self-reported user feedback can include information indicative of a self-reported subjective sleep score (e.g., poor, average, excellent), a self-reported subjective stress level of the user, a self-reported subjective fatigue level of the user, a self-reported subjective health status of the user, a recent life event experienced by the user, or any combination thereof.

The electronic interface 119 is configured to receive data (e.g., physiological data and/or acoustic data) from the one or more sensors 130 such that the data can be stored in the memory device 114 and/or analyzed by the processor 112 of the control system 110. The electronic interface 119 can communicate with the one or more sensors 130 using a wired connection or a wireless connection (e.g., using an RF communication protocol, a WiFi communication protocol, a Bluetooth communication protocol, an IR communication protocol, over a cellular network, over any other optical communication protocol, etc.). The electronic interface 119 can include an antenna, a receiver (e.g., an RF receiver), a transmitter (e.g., an RF transmitter), a transceiver, or any combination thereof. The electronic interface 119 can also include one more processors and/or one more memory devices that are the same as, or similar to, the processor 112 and the memory device 114 described herein. In some implementations, the electronic interface 119 is coupled to or integrated in the external device 170. In other implementations, the electronic interface 119 is coupled to or integrated (e.g., in a housing) with the control system 110 and/or the memory device 114.

As noted above, in some implementations, the system 100 optionally includes the respiratory therapy system 120 (also referred to as a respiratory pressure therapy system). The respiratory therapy system 120 can include the respiratory therapy device 122 (also referred to as a respiratory pressure therapy device), a user interface 124, a conduit 126 (also referred to as a tube or an air circuit), a display device 128, a humidification tank 129, or any combination thereof. In some implementations, the control system 110, the memory device 114, the display device 128, one or more of the sensors 130, and the humidification tank 129 are part of the respiratory therapy device 122. Respiratory pressure therapy refers to the application of a supply of air to an entrance to a user's airways at a controlled target pressure that is nominally positive with respect to atmosphere throughout the user's breathing cycle (e.g., in contrast to negative pressure therapies such as the tank ventilator or cuirass). The respiratory therapy system 120 is generally used to treat individuals suffering from one or more sleep-related respiratory disorders (e.g., obstructive sleep apnea, central sleep apnea, or mixed sleep apnea), other respiratory disorders such as COPD, or other disorders leading to respiratory insufficiency, that may manifest either during sleep or wakefulness.

The respiratory therapy device 122 is generally used to generate pressurized air that is delivered to a user (e.g., using one or more motors that drive one or more compressors). In some implementations, the respiratory therapy device 122 generates continuous constant air pressure that is delivered to the user. In other implementations, the respiratory therapy device 122 generates two or more predetermined pressures (e.g., a first predetermined air pressure and a second predetermined air pressure). In still other implementations, the respiratory therapy device 122 is configured to generate a variety of different air pressures within a predetermined range. For example, the respiratory therapy device 122 can deliver at least about 6 cm $H_2O$, at least about 10 cm $H_2O$, at least about 20 cm $H_2O$, between about 6 cm $H_2O$ and about 10 cm $H_2O$, between about 7 cm $H_2O$ and about 12 cm $H_2O$, etc. The respiratory therapy device 122 can also deliver pressurized air at a predetermined flow rate between, for example, about −20 L/min and about 150 L/min, while maintaining a positive pressure (relative to the ambient pressure). In some implementations, the control system 110, the memory device 114, the electronic interface 119, or any combination thereof can be coupled to and/or positioned within a housing of the respiratory therapy device 122.

The user interface 124 engages a portion of the user's face and delivers pressurized air from the respiratory therapy device 122 to the user's airway to aid in preventing the airway from narrowing and/or collapsing during sleep. This may also increase the user's oxygen intake during sleep. Depending upon the therapy to be applied, the user interface 124 may form a seal, for example, with a region or portion of the user's face, to facilitate the delivery of gas at a pressure at sufficient variance with ambient pressure to effect therapy, for example, at a positive pressure of about 10 cm $H_2O$ relative to ambient pressure. For other forms of therapy, such as the delivery of oxygen, the user interface may not include a seal sufficient to facilitate delivery to the airways of a supply of gas at a positive pressure of about 10 cm $H_2O$.

Figure 2:
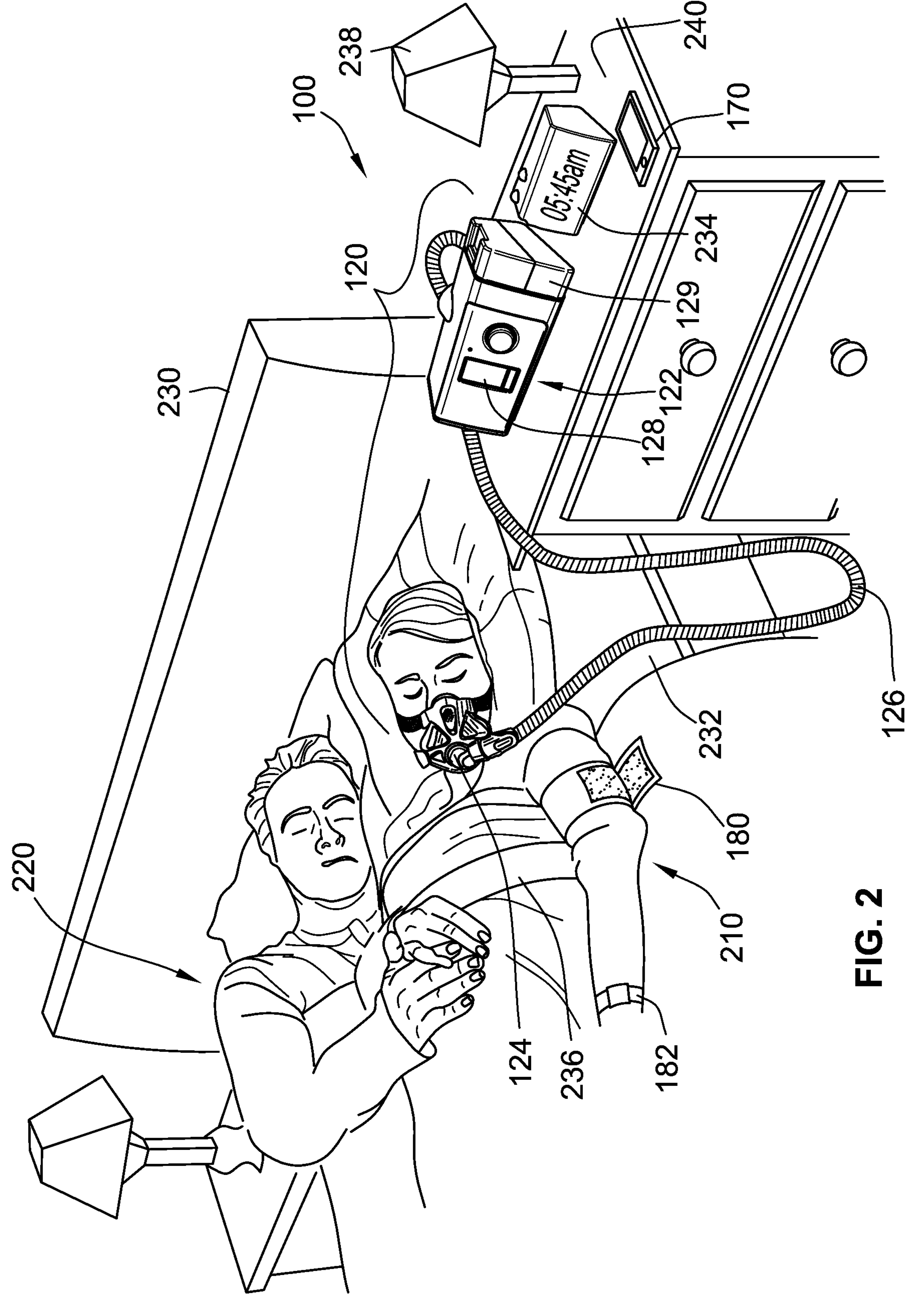
FIG. 2 is a perspective view of the system of FIG. 1, a user of the system, and a bed partner of the user, according to some implementations of the present disclosure.

In some implementations, the user interface 124 is or includes a facial mask that covers the nose and mouth of the user (as shown, for example, in FIG. 2). Alternatively, the user interface 124 is or includes a nasal mask that provides air to the nose of the user or a nasal pillow mask that delivers air directly to the nostrils of the user. The user interface 124 can include a strap assembly that has a plurality of straps (e.g., including hook and loop fasteners) for positioning and/or stabilizing the user interface 124 on a portion of the user interface 124 on a desired location of the user (e.g., the face), and a conformal cushion (e.g., silicone, plastic, foam, etc.) that aids in providing an air-tight seal between the user interface 124 and the user. The user interface 124 can also include one or more vents 125 for permitting the escape of carbon dioxide and other gases exhaled by the user. In other implementations, the user interface 124 includes a mouthpiece (e.g., a night guard mouthpiece molded to conform to the user's teeth, a mandibular repositioning device, etc.).

The conduit 126 allows the flow of air between two components of the respiratory therapy system 120, such as the respiratory therapy device 122 and the user interface 124. In some implementations, there can be separate limbs of the conduit for inhalation and exhalation. In other implementations, a single limb conduit is used for both inhalation and exhalation. Generally, the respiratory therapy system 120 forms an air pathway that extends between a motor of the respiratory therapy device 122 and the user and/or the user's airway. Thus, the air pathway generally includes at least a motor of the respiratory therapy device 122, the user interface 124, and the conduit 126.

One or more of the respiratory therapy device 122, the user interface 124, the conduit 126, the display device 128, and the humidification tank 129 can contain one or more sensors (e.g., a pressure sensor, a flow rate sensor, or more generally any of the other sensors 130 described herein). These one or more sensors can be used, for example, to measure the air pressure and/or flow rate of pressurized air supplied by the respiratory therapy device 122.

The display device 128 is generally used to display image(s) including still images, video images, or both and/or information regarding the respiratory therapy device 122. For example, the display device 128 can provide information regarding the status of the respiratory therapy device 122 (e.g., whether the respiratory therapy device 122 is on/off, the pressure of the air being delivered by the respiratory therapy device 122, the temperature of the air being delivered by the respiratory therapy device 122, etc.) and/or other information (e.g., a sleep score or a therapy score (also referred to as a myAir™ score, such as described in WO 2016/061629, which is hereby incorporated by reference herein in its entirety), the current date/time, personal information for the user, etc.). In some implementations, the display device 128 acts as a human-machine interface (HMI) that includes a graphic user interface (GUI) configured to display the image(s) as an input interface. The display device 128 can be an LED display, an OLED display, an LCD display, or the like. The input interface can be, for example, a touchscreen or touch-sensitive substrate, a mouse, a keyboard, or any sensor system configured to sense inputs made by a human user interacting with the respiratory therapy device 122.

The humidification tank 129 is coupled to or integrated in the respiratory therapy device 122 and includes a reservoir of water that can be used to humidify the pressurized air delivered from the respiratory therapy device 122. The respiratory therapy device 122 can include a heater to heat the water in the humidification tank 129 in order to humidify the pressurized air provided to the user. Additionally, in some implementations, the conduit 126 can also include a heating element (e.g., coupled to and/or imbedded in the conduit 126) that heats the pressurized air delivered to the user. In other implementations, the respiratory therapy device 122 or the conduit 126 can include a waterless humidifier. The waterless humidifier can incorporate sensors that interface with other sensor positioned elsewhere in the system 100.

The respiratory therapy system 120 can be used, for example, as a ventilator or a positive airway pressure (PAP) system, such as a continuous positive airway pressure (CPAP) system, an automatic positive airway pressure system (APAP), a bi-level or variable positive airway pressure system (BPAP or VPAP), or any combination thereof. The CPAP system delivers a predetermined air pressure (e.g., determined by a sleep physician) to the user. The APAP system automatically varies the air pressure delivered to the user based at least in part on, for example, respiration data associated with the user. The BPAP or VPAP system is configured to deliver a first predetermined pressure (e.g., an inspiratory positive airway pressure or IPAP) and a second predetermined pressure (e.g., an expiratory positive airway pressure or EPAP) that is lower than the first predetermined pressure.

The DEB mitigation system 184 is configured to perform actions that can aid in mitigating any DEB that the user experiences during the sleep session. The DEB mitigation system 184 can include an alarm 186, a light 188, a bed adjustment mechanism 190, a physical contact mechanism 192, a barrier 194, or any combination thereof. Episodes of DEB can often include sudden and potentially violent movements that have the potential to injure the user or the user's bed partner. And even certain vocalizations can cause the user harm, for example yelling at high volumes. The DEB mitigation system 184 can wake the user up to stop the DEB episode, or can take other actions to mitigate the impact of the DEB on the user or their bed partner. As shown in FIG. 1, the DEB mitigation system 184 includes a variety of different devices or components that can mitigate or end the DEB episode.

The alarm 186 is any audible noise that is configured to wake the user up, or interrupt the user's sleep to reduce the severity of the DEB. The alarm 186 can be implemented on a standalone alarm clock, a speaker (such as an Internet-connected smart speaker), on the external device 170 (which could be a mobile device such as a mobile phone or tablet computer), or any other suitable device. The alarm 186 can produce an alarm-like noise (e.g., a ringing noise, a siren noise, etc.), but can also be configured to play music, nature sounds, spoken words, or other soothing sounds. Generally, the alarm 186 has a volume level sufficient to wake the user up from the sleep session, but in some implementations, the volume level of the alarm 186 may be selected such that when the alarm 186 is activated, the user exits the atypical REM sleep and enters one of the other sleep stages.

The light 188 that is configured to activate and either cause the user to wake up, or cause the user to exit the atypical REM sleep stage. The light 188 can be a light on the external device 170 (e.g., a flashlight on the user's phone or the display device 172 itself), a separate light in the user's bedroom (e.g., ceiling lights or a lamp), or could be a light on a standalone alarm clock that includes the alarm 186.

The bed adjustment mechanism 190 is configured to adjust the user's bed or a portion of the user's bed, in order to wake the user up, stop the user's DEB. In some implementations, the bed adjustment mechanism 190 is configured to vibrate the user's bed or a portion of the user's bed, when activated. This vibration can be accomplished using a vibration or massage function of the bed on which the user is sleeping. In other implementations, the vibration could be accomplished a vibrating pad or other device that the user lays on during the sleep session. In other implementations, the bed adjustment mechanism 190 includes a motor or other similar device that can incline or decline the user's bed. When the bed adjustment mechanism 190 is activated, the physical movement of the bed causes the user to either wake up, or interrupts the sleep session enough so that the user exits the atypical REM sleep stage, thus ending the DEB.

The physical contact mechanism 192 can be any mechanism that physically contacts the user. The physical contact mechanism 192 can be used to end or mitigate the user's DEB by waking the user up or causing the user to exit the atypical REM sleep stage. For example, the physical contact mechanism 192 can be some type of actuator that when activated, contacts the user. The physical contact mechanism 192 could also be a fan that is configured to blow air onto the user to aid in waking the user up, or interrupting the sleep session to a sufficient degree so that the user exits the atypical REM sleep stage, thus ending the DEB.

In some implementations, the physical contact mechanism 192 is additionally or alternatively used to physically prevent harm from coming to the user or the user's bed partner while the user is experiencing DEB. In one example, the physical contact mechanism 192 is a strap that extends over and/or around at least a portion of the user. The strap can be tightened when the system 100 detects that DEB is occurring. A strap positioned over the user's arms can prevent the user's arms from moving or punching, and potentially striking the user's bed partner or other solid objects, such as the bedframe or a bedside table. The strap could also be positioned over the user's legs to prevent the user from kicking the user's bed partner or another object. The tightening of the strap could also be implemented with the user's bedsheets or a blanket. Generally, the user will be sleeping underneath bedsheets and/or a blanket. The bedsheets and/or blanket can be connected to a device (such as a motor) that can cause the bedsheets and/or blanket to tighten around the user, which can prevent the user from punching or kicking, and harming themselves or their bed partner.

Finally, the barrier 194 can be activated to provide protection for one or both of the user and the user's bed partner. In some implementations, the barrier 194 is positioned between the user and the bed partner, and when DEB is detected, the barrier 194 is moved to a position designed to prevent the user from accidentally striking the bed partner. In some implementations, the position is a raised position such that the barrier 194 separates the user and the user's bed partner. The barrier 194 (or an additional barrier 194) could also be placed between the user and the side of the bed, which could be used to prevent the user from striking a bedside table, or even from falling out of the bed.

Generally, the system 100 can include any one or more of the illustrated components of the DEB mitigation system 184. The DEB mitigation system 184 can additionally or alternatively include other components as well. In any implementation, the DEB mitigation system 184 can aid in ending the DEB, for example by waking the user up or causing the user to exit the atypical REM sleep stage. The DEB mitigation system 184 can also be used to mitigate the impact of the DEB on the user and/or the user's bed partner, for example by reducing the user's movement or preventing the user from moving at all, or by providing a degree of physical protection to the user and/or the user's bed partner.

Referring to FIG. 2, a portion of the system 100 (FIG. 1), according to some implementations, is illustrated. A user 210 of the respiratory therapy system 120 and a bed partner 220 are located in a bed 230 and are laying on a mattress 232. The user interface 124 (e.g., a full facial mask) can be worn by the user 210 during a sleep session. The user interface 124 is fluidly coupled and/or connected to the respiratory therapy device 122 via the conduit 126. In turn, the respiratory therapy device 122 delivers pressurized air to the user 210 via the conduit 126 and the user interface 124 to increase the air pressure in the throat of the user 210 to aid in preventing the airway from closing and/or narrowing during sleep. The respiratory therapy device 122 can include the display device 128, which can allow the user to interact with the respiratory therapy device 122. The respiratory therapy device 122 can also include the humidification tank 129, which stores the water used to humidify the pressurized air. The respiratory therapy device 122 can be positioned on a nightstand 240 that is directly adjacent to the bed 230 as shown in FIG. 2, or more generally, on any surface or structure that is generally adjacent to the bed 230 and/or the user 210. The user can also wear the blood pressure device 180 and the activity tracker 182 while lying on the mattress 232 in the bed 230.

An alarm clock 234 and a lamp 238 are also positioned on the nightstand 240. The alarm clock 234 can be used to implement one or both of the alarm 186 and the light 188 of the DEB mitigation system 184 (FIG. 1). The light 188 of the DEB mitigation system 184 can additionally or alternatively be implemented using the lamp 238. FIG. 2 also shows a strap 236 placed over the user. The strap 236 can be used as the physical contact mechanism 192 of the DEB mitigation system 184. The strap 236 is shown as being placed over the user 210's torso, but could alternatively be placed over the user 210's arms or the user 210's legs.

FIG. 2 shows the system 100 with both the respiratory therapy system 120 and the components of the DEB mitigation system 184. However, in some implementations, the user 210 may use the DEB mitigation system 184 without also using the respiratory therapy system 120. For example, the user 210 may not suffer from any sleep-related and/or respiratory-related disorders (such as OSA) that require the use of the respiratory therapy system 120. However, the user 210 may still suffer from RBD, in which case components of the DEB mitigation system 184 can be utilized.

Referring back to FIG. 1, the one or more sensors 130 of the system 100 include a pressure sensor 132, a flow rate sensor 134, a temperature sensor 136, a motion sensor 138, a microphone 140, a speaker 142, a radio-frequency (RF) receiver 146, an RF transmitter 148, a camera 150, an infrared (IR) sensor 152, a photoplethysmogram (PPG) sensor 154, an electrocardiogram (ECG) sensor 156, an electroencephalography (EEG) sensor 158, a capacitive sensor 160, a force sensor 162, a strain gauge sensor 164, an electromyography (EMG) sensor 166, an oxygen sensor 168, an analyte sensor 174, a moisture sensor 176, a light detection and ranging (LiDAR) sensor 178, or any combination thereof. Generally, each of the one or sensors 130 are configured to output sensor data that is received and stored in the memory device 114 or one or more other memory devices. The sensors 130 can also include, an electrooculography (EOG) sensor, a peripheral oxygen saturation ($SpO_2$) sensor, a galvanic skin response (GSR) sensor, a carbon dioxide ($CO_2$) sensor, or any combination thereof.

While the one or more sensors 130 are shown and described as including each of the pressure sensor 132, the flow rate sensor 134, the temperature sensor 136, the motion sensor 138, the microphone 140, the speaker 142, the RF receiver 146, the RF transmitter 148, the camera 150, the IR sensor 152, the PPG sensor 154, the ECG sensor 156, the EEG sensor 158, the capacitive sensor 160, the force sensor 162, the strain gauge sensor 164, the EMG sensor 166, the oxygen sensor 168, the analyte sensor 174, the moisture sensor 176, and the LiDAR sensor 178, more generally, the one or more sensors 130 can include any combination and any number of each of the sensors described and/or shown herein.

The one or more sensors 130 can be used to generate, for example physiological data, acoustic data, or both, that is associated with a user of the respiratory therapy system 120 (such as the user 210 of FIG. 2), the respiratory therapy system 120, both the user and the respiratory therapy system 120, or other entities, objects, activities, etc. Physiological data generated by one or more of the sensors 130 can be used by the control system 110 to determine a sleep-wake signal associated with the user during the sleep session and one or more sleep-related parameters. The sleep-wake signal can be indicative of one or more sleep stages and/or sleep states (which can be used interchangeably herein), including sleep, wakefulness, relaxed wakefulness, micro-awakenings, or distinct sleep stages such as a rapid eye movement (REM) stage (which can include both a typical REM stage and an atypical REM stage), a first non-REM stage (often referred to as "N1"), a second non-REM stage (often referred to as "N2"), a third non-REM stage (often referred to as "N3"), or any combination thereof. Methods for determining sleep stages and/or sleep states from physiological data generated by one or more of the sensors, such as sensors 130, and for methods for training algorithms for determining sleep stages and/or sleep states, are described in, for example, WO 2014/047310, US 2014/0088373, WO 2017/132726, WO 2019/122413, and WO 2019/122414, each of which is hereby incorporated by reference herein in its entirety.

The sleep-wake signal can also be timestamped to indicate a time that the user enters the bed, a time that the user exits the bed, a time that the user attempts to fall asleep, etc. The sleep-wake signal can be measured one or more of the sensors 130 during the sleep session at a predetermined sampling rate, such as, for example, one sample per second, one sample per 30 seconds, one sample per minute, etc. Examples of the one or more sleep-related parameters that can be determined for the user during the sleep session based at least in part on the sleep-wake signal include a total time in bed, a total sleep time, a total wake time, a sleep onset latency, a wake-after-sleep-onset parameter, a sleep efficiency, a fragmentation index, an amount of time to fall asleep, a consistency of breathing rate, a fall asleep time, a wake time, a rate of sleep disturbances, a number of movements, or any combination thereof.

Physiological data and/or acoustic data generated by the one or more sensors 130 can also be used to determine a respiration signal associated with the user during a sleep session. the respiration signal is generally indicative of respiration or breathing of the user during the sleep session. The respiration signal can be indicative of, for example, a respiration rate, a respiration rate variability, an inspiration amplitude, an expiration amplitude, an inspiration-expiration amplitude ratio, an inspiration-expiration duration ratio, a number of events per hour, a pattern of events, pressure settings of the respiratory therapy device 122, or any combination thereof. The event(s) can include snoring, apneas, central apneas, obstructive apneas, mixed apneas, hypopneas, a mask leak (e.g., from the user interface 124), a restless leg, a sleeping disorder, choking, an increased heart rate, a heart rate variation, labored breathing, an asthma attack, an epileptic episode, a seizure, a fever, a cough, a sneeze, a snore, a gasp, the presence of an illness such as the common cold or the flu, an elevated stress level, etc.

The pressure sensor 132 outputs pressure data that can be stored in the memory device 114 and/or analyzed by the processor 112 of the control system 110. In some implementations, the pressure sensor 132 is an air pressure sensor (e.g., barometric pressure sensor) that generates sensor data indicative of the respiration (e.g., inhaling and/or exhaling) of the user of the respiratory therapy system 120 and/or ambient pressure. In such implementations, the pressure sensor 132 can be coupled to or integrated in the respiratory therapy device 122. The pressure sensor 132 can be, for example, a capacitive sensor, an electromagnetic sensor, an inductive sensor, a resistive sensor, a piezoelectric sensor, a strain-gauge sensor, an optical sensor, a potentiometric sensor, or any combination thereof. In one example, the pressure sensor 132 can be used to determine a blood pressure of the user.

The flow rate sensor 134 outputs flow rate data that can be stored in the memory device 114 and/or analyzed by the processor 112 of the control system 110. In some implementations, the flow rate sensor 134 is used to determine an air flow rate from the respiratory therapy device 122, an air flow rate through the conduit 126, an air flow rate through the user interface 124, or any combination thereof. In such implementations, the flow rate sensor 134 can be coupled to or integrated in the respiratory therapy device 122, the user interface 124, or the conduit 126. The flow rate sensor 134 can be a mass flow rate sensor such as, for example, a rotary flow meter (e.g., Hall effect flow meters), a turbine flow meter, an orifice flow meter, an ultrasonic flow meter, a hot wire sensor, a vortex sensor, a membrane sensor, or any combination thereof.

The temperature sensor 136 outputs temperature data that can be stored in the memory device 114 and/or analyzed by the processor 112 of the control system 110. In some implementations, the temperature sensor 136 generates temperatures data indicative of a core body temperature of the user, a skin temperature of the user, a temperature of the air flowing from the respiratory therapy device 122 and/or through the conduit 126, a temperature in the user interface 124, an ambient temperature, or any combination thereof. The temperature sensor 136 can be, for example, a thermocouple sensor, a thermistor sensor, a silicon band gap temperature sensor or semiconductor-based sensor, a resistance temperature detector, or any combination thereof.

The motion sensor 138 outputs motion data that can be stored in the memory device 114 and/or analyzed by the processor 112 of the control system 110. The motion sensor 138 can be used to detect movement of the user during the sleep session, and/or detect movement of any of the components of the respiratory therapy system 120, such as the respiratory therapy device 122, the user interface 124, or the conduit 126. The motion sensor 138 can include one or more inertial sensors, such as accelerometers, gyroscopes, and magnetometers. The motion sensor 138 can be used to detect motion or acceleration associated with arterial pulses, such as pulses in or around the face of the user and proximal to the user interface 124, and configured to detect features of the pulse shape, speed, amplitude, or volume.

The microphone 140 outputs acoustic data that can be stored in the memory device 114 and/or analyzed by the processor 112 of the control system 110. The acoustic data generated by the microphone 140 is reproducible as one or more sound(s) during a sleep session (e.g., sounds from the user) to determine (e.g., using the control system 110) one or more sleep-related parameters, as described in further detail herein. The acoustic data from the microphone 140 can also be used to identify (e.g., using the control system 110) an event experienced by the user during the sleep session, as described in further detail herein. In other implementations, the acoustic data from the microphone 140 is representative of noise associated with the respiratory therapy system 120. The microphone 140 can be coupled to or integrated in the respiratory therapy system 120 (or the system 100) generally in any configuration. For example, the microphone 140 can be disposed inside the respiratory therapy device 122, the user interface 124, the conduit 126, or other components. The microphone 140 can also be positioned adjacent to or coupled to the outside of the respiratory therapy device 122, the outside of the user interface 124, the outside of the conduit 126, or outside of any other components. The microphone 140 could also be a component of the external device 170 (e.g., the microphone 140 is a microphone of a smart phone). The microphone 140 can be integrated into the user interface 124, the conduit 126, the respiratory therapy device 122, or any combination thereof. In general, the microphone 140 can be located at any point within or adjacent to the air pathway of the respiratory therapy system 120, which includes at least the motor of the respiratory therapy device 122, the user interface 124, and the conduit 126. Thus, the air pathway can also be referred to as the acoustic pathway.

The speaker 142 outputs sound waves that are audible to the user. The speaker 142 can be used, for example, as an alarm clock or to play an alert or message to the user (e.g., in response to an event). In some implementations, the speaker 142 can be used to communicate the acoustic data generated by the microphone 140 to the user. The speaker 142 can be coupled to or integrated in the respiratory therapy device 122, the user interface 124, the conduit 126, or the external device 170.

The microphone 140 and the speaker 142 can be used as separate devices. In some implementations, the microphone 140 and the speaker 142 can be combined into an acoustic sensor 141 (e.g., a SONAR sensor), as described in, for example, WO 2018/050913 and WO 2020/104465, each of which is hereby incorporated by reference herein in its entirety. In such implementations, the speaker 142 generates or emits sound waves at a predetermined interval and/or frequency, and the microphone 140 detects the reflections of the emitted sound waves from the speaker 142. The sound waves generated or emitted by the speaker 142 have a frequency that is not audible to the human ear (e.g., below 20 Hz or above around 18 kHz) so as not to disturb the sleep of the user or a bed partner of the user (such as bed partner 220 in FIG. 2). Based at least in part on the data from the microphone 140 and/or the speaker 142, the control system 110 can determine a location of the user and/or one or more of the sleep-related parameters described in herein, such as, for example, a respiration signal, a respiration rate, an inspiration amplitude, an expiration amplitude, an inspiration-expiration ratio, a number of events per hour, a pattern of events, a sleep stage, pressure settings of the respiratory therapy device 122, or any combination thereof. In this context, a SONAR sensor may be understood to concern an active acoustic sensing, such as by generating/transmitting ultrasound or low frequency ultrasound sensing signals (e.g., in a frequency range of about 17-23 kHz, 18-22 kHz, or 17-18 kHz, for example), through the air. Such a system may be considered in relation to WO 2018/050913 and WO 2020/104465 mentioned above. In some implementations, the speaker 142 is a bone conduction speaker. In some implementations, the one or more sensors 130 include (i) a first microphone that is the same or similar to the microphone 140, and is integrated into the acoustic sensor 141 and (ii) a second microphone that is the same as or similar to the microphone 140, but is separate and distinct from the first microphone that is integrated into the acoustic sensor 141.

The RF transmitter 148 generates and/or emits radio waves having a predetermined frequency and/or a predetermined amplitude (e.g., within a high frequency band, within a low frequency band, long wave signals, short wave signals, etc.). The RF receiver 146 detects the reflections of the radio waves emitted from the RF transmitter 148, and this data can be analyzed by the control system 110 to determine a location of the user and/or one or more of the sleep-related parameters described herein. An RF receiver (either the RF receiver 146 and the RF transmitter 148 or another RF pair) can also be used for wireless communication between the control system 110, the respiratory therapy device 122, the one or more sensors 130, the external device 170, or any combination thereof. While the RF receiver 146 and RF transmitter 148 are shown as being separate and distinct elements in FIG. 1, in some implementations, the RF receiver 146 and RF transmitter 148 are combined as a part of an RF sensor 147 (e.g., a RADAR sensor). In some such implementations, the RF sensor 147 includes a control circuit. The specific format of the RF communication could be WiFi, Bluetooth, etc.

In some implementations, the RF sensor 147 is a part of a mesh system. One example of a mesh system is a WiFi mesh system, which can include mesh nodes, mesh router(s), and mesh gateway(s), each of which can be mobile/movable or fixed. In such implementations, the WiFi mesh system includes a WiFi router and/or a WiFi controller and one or more satellites (e.g., access points), each of which include an RF sensor that the is the same as, or similar to, the RF sensor 147. The WiFi router and satellites continuously communicate with one another using WiFi signals. The WiFi mesh system can be used to generate motion data based at least in part on changes in the WiFi signals (e.g., differences in received signal strength) between the router and the satellite(s) due to an object or person moving partially obstructing the signals. The motion data can be indicative of motion, breathing, heart rate, gait, falls, behavior, etc., or any combination thereof.

The camera 150 outputs image data reproducible as one or more images (e.g., still images, video images, thermal images, or a combination thereof) that can be stored in the memory device 114. The image data from the camera 150 can be used by the control system 110 to determine one or more of the sleep-related parameters described herein. For example, the image data from the camera 150 can be used to identify a location of the user, to determine a time when the user enters the user's bed (such as bed 230 in FIG. 2), and to determine a time when the user exits the bed 230. The camera 150 can also be used to track eye movements, pupil dilation (if one or both of the user's eyes are open), blink rate, or any changes during REM sleep. The camera 150 can also be used to track the position of the user, which can impact the duration and/or severity of apneic episodes in users with positional obstructive sleep apnea.

The IR sensor 152 outputs infrared image data reproducible as one or more infrared images (e.g., still images, video images, or both) that can be stored in the memory device 114. The infrared data from the IR sensor 152 can be used to determine one or more sleep-related parameters during the sleep session, including a temperature of the user and/or movement of the user. The IR sensor 152 can also be used in conjunction with the camera 150 when measuring the presence, location, and/or movement of the user. The IR sensor 152 can detect infrared light having a wavelength between about 700 nm and about 1 mm, for example, while the camera 150 can detect visible light having a wavelength between about 380 nm and about 740 nm.

The IR sensor 152 outputs infrared image data reproducible as one or more infrared images (e.g., still images, video images, or both) that can be stored in the memory device 114. The infrared data from the IR sensor 152 can be used to determine one or more sleep-related parameters during the sleep session, including a temperature of the user and/or movement of the user, including movement associated with RBD or DEB. The IR sensor 152 can also be used in conjunction with the camera 150 when measuring the presence, location, and/or movement of the user. The IR sensor 152 can detect infrared light having a wavelength between about 700 nm and about 1 mm, for example, while the camera 150 can detect visible light having a wavelength between about 380 nm and about 740 nm.

The PPG sensor 154 outputs physiological data associated with the user that can be used to determine one or more sleep-related parameters, such as, for example, a heart rate, a heart rate pattern, a heart rate variability, a cardiac cycle, respiration rate, an inspiration amplitude, an expiration amplitude, an inspiration-expiration ratio, estimated blood pressure parameter(s), or any combination thereof. The PPG sensor 154 can be worn by the user, embedded in clothing and/or fabric that is worn by the user, embedded in and/or coupled to the user interface 124 and/or its associated headgear (e.g., straps, etc.), etc.

The ECG sensor 156 outputs physiological data associated with electrical activity of the heart of the user. In some implementations, the ECG sensor 156 includes one or more electrodes that are positioned on or around a portion of the user during the sleep session. The physiological data from the ECG sensor 156 can be used, for example, to determine one or more of the sleep-related parameters described herein.

The EEG sensor 158 outputs physiological data associated with electrical activity of the brain of the user. In some implementations, the EEG sensor 158 includes one or more electrodes that are positioned on or around the scalp of the user during the sleep session. The physiological data from the EEG sensor 158 can be used, for example, to determine a sleep stage and/or a sleep state of the user at any given time during the sleep session. In some implementations, the EEG sensor 158 can be integrated in the user interface 124 and/or the associated headgear (e.g., straps, etc.).

The capacitive sensor 160, the force sensor 162, and the strain gauge sensor 164 output data that can be stored in the memory device 114 and used by the control system 110 to determine one or more of the sleep-related parameters described herein. The EMG sensor 166 outputs physiological data associated with electrical activity produced by one or more muscles. The oxygen sensor 168 outputs oxygen data indicative of an oxygen concentration of gas (e.g., in the conduit 126 or at the user interface 124). The oxygen sensor 168 can be, for example, an ultrasonic oxygen sensor, an electrical oxygen sensor, a chemical oxygen sensor, an optical oxygen sensor, or any combination thereof. In some implementations, the one or more sensors 130 also include a galvanic skin response (GSR) sensor, a blood flow sensor, a respiration sensor, a pulse sensor, a sphygmomanometer sensor, an oximetry sensor, or any combination thereof.

The analyte sensor 174 can be used to detect the presence of an analyte in the exhaled breath of the user. The data output by the analyte sensor 174 can be stored in the memory device 114 and used by the control system 110 to determine the identity and concentration of any analytes in the user's breath. In some implementations, the analyte sensor 174 is positioned near a mouth of the user to detect analytes in breath exhaled from the user's mouth. For example, when the user interface 124 is a facial mask that covers the nose and mouth of the user, the analyte sensor 174 can be positioned within the facial mask to monitor the user mouth breathing. In other implementations, such as when the user interface 124 is a nasal mask or a nasal pillow mask, the analyte sensor 174 can be positioned near the nose of the user to detect analytes in breath exhaled through the user's nose. In still other implementations, the analyte sensor 174 can be positioned near the user's mouth when the user interface 124 is a nasal mask or a nasal pillow mask. In this implementation, the analyte sensor 174 can be used to detect whether any air is inadvertently leaking from the user's mouth. In some implementations, the analyte sensor 174 is a volatile organic compound (VOC) sensor that can be used to detect carbon-based chemicals or compounds, such as carbon dioxide. In some implementations, the analyte sensor 174 can also be used to detect whether the user is breathing through their nose or mouth. For example, if the data output by an analyte sensor 174 positioned near the mouth of the user or within the facial mask (in implementations where the user interface 124 is a facial mask) detects the presence of an analyte, the control system 110 can use this data as an indication that the user is breathing through their mouth.

The moisture sensor 176 outputs data that can be stored in the memory device 114 and used by the control system 110. The moisture sensor 176 can be used to detect moisture in various areas surrounding the user (e.g., inside the conduit 126 or the user interface 124, near the user's face, near the connection between the conduit 126 and the user interface 124, near the connection between the conduit 126 and the respiratory therapy device 122, etc.). Thus, in some implementations, the moisture sensor 176 can be coupled to or integrated into the user interface 124 or in the conduit 126 to monitor the humidity of the pressurized air from the respiratory therapy device 122. In other implementations, the moisture sensor 176 is placed near any area where moisture levels need to be monitored. The moisture sensor 176 can also be used to monitor the humidity of the ambient environment surrounding the user, for example the air inside the user's bedroom. The moisture sensor 176 can also be used to track the user's biometric response to environmental changes.

One or more LiDAR sensors 178 can be used for depth sensing. This type of optical sensor (e.g., laser sensor) can be used to detect objects and build three dimensional (3D) maps of the surroundings, such as of a living space. LiDAR can generally utilize a pulsed laser to make time of flight measurements. LiDAR is also referred to as 3D laser scanning. In an example of use of such a sensor, a fixed or mobile device (such as a smartphone) having a LiDAR sensor 178 can measure and map an area extending 5 meters or more away from the sensor. The LiDAR data can be fused with point cloud data estimated by an electromagnetic RADAR sensor, for example. The LiDAR sensor 178 may also use artificial intelligence (AI) to automatically geofence RADAR systems by detecting and classifying features in a space that might cause issues for RADAR systems, such a glass windows (which can be highly reflective to RADAR). LiDAR can also be used to provide an estimate of the height of a person, as well as changes in height when the person sits down, or falls down, for example. LiDAR may be used to form a 3D mesh representation of an environment. In a further use, for solid surfaces through which radio waves pass (e.g., radio-translucent materials), the LiDAR may reflect off such surfaces, thus allowing a classification of different type of obstacles.

While shown separately in FIG. 1, any combination of the one or more sensors 130 can be integrated in and/or coupled to any one or more of the components of the system 100, including the respiratory therapy device 122, the user interface 124, the conduit 126, the humidification tank 129, the control system 110, the external device 170, the DEB mitigation system 184, or any combination thereof. For example, the acoustic sensor 141 and/or the RF sensor 147 can be integrated in and/or coupled to the external device 170. In such implementations, the external device 170 can be considered a secondary device that generates additional or secondary data for use by the system 100 (e.g., the control system 110) according to some aspects of the present disclosure. In some implementations, the pressure sensor 132 and/or the flow rate sensor 134 are integrated into and/or coupled to the respiratory therapy device 122. In some implementations, at least one of the one or more sensors 130 is not coupled to the respiratory therapy device 122, the control system 110, or the external device 170, and is positioned generally adjacent to the user during the sleep session (e.g., positioned on or in contact with a portion of the user, worn by the user, coupled to or positioned on the nightstand, coupled to the mattress, coupled to the ceiling, etc.). More generally, the one or more sensors 130 can be positioned at any suitable location relative to the user such that the one or more sensors 130 can generate physiological data associated with the user and/or the bed partner 220 during one or more sleep session.

The data from the one or more sensors 130 can be analyzed to determine one or more sleep-related parameters, which can include a respiration signal, a respiration rate, a respiration pattern, an inspiration amplitude, an expiration amplitude, bodily movement (e.g., gross bodily movement such as movement of one or more limbs, fine bodily movement such as movement of the chest, movement in bed, etc.), an inspiration-expiration ratio, an occurrence of one or more events, a number of events per hour, a pattern of events, an average duration of events, a range of event durations, a ratio between the number of different events, a sleep stage, an apnea-hypopnea index (AHI), or any combination thereof. The one or more events can include snoring, apneas, central apneas, obstructive apneas, mixed apneas, hypopneas, an intentional user interface leak, an unintentional user interface leak, a mouth leak, a cough, a restless leg, a sleeping disorder, choking, an increased heart rate, labored breathing, an asthma attack, an epileptic episode, a seizure, increased blood pressure, or any combination thereof. Many of these sleep-related parameters are physiological parameters, although some of the sleep-related parameters can be considered to be non-physiological parameters. Other types of physiological and non-physiological parameters can also be determined, either from the data from the one or more sensors 130, or from other types of data.

The external device 170 includes a display device 172. The external device 170 can be, for example, a mobile device such as a smart phone, a tablet, a laptop, or the like. Alternatively, the external device 170 can be an external sensing system, a television (e.g., a smart television) or another smart home device (e.g., a smart speaker(s) such as Google Home, Amazon Echo, Alexa etc.). In some implementations, the external device 170 is a wearable device (e.g., a smart watch). The display device 172 is generally used to display image(s) including still images, video images, or both. In some implementations, the display device 172 acts as a human-machine interface (HMI) that includes a graphic user interface (GUI) configured to display the image(s) and an input interface. The display device 172 can be an LED display, an OLED display, an LCD display, or the like. The input interface can be, for example, a touchscreen or touch-sensitive substrate, a mouse, a keyboard, or any sensor system configured to sense inputs made by a human user interacting with the external device 170. In some implementations, one or more external devices 170 can be used by and/or included in the system 100.

The blood pressure device 180 is generally used to aid in generating physiological data for determining one or more blood pressure measurements associated with a user. The blood pressure device 180 can include at least one of the one or more sensors 130 to measure, for example, a systolic blood pressure component and/or a diastolic blood pressure component.

In some implementations, the blood pressure device 180 is a sphygmomanometer including an inflatable cuff that can be worn by a user and a pressure sensor (e.g., the pressure sensor 132 described herein). For example, as shown in the example of FIG. 2, the blood pressure device 180 can be worn on an upper arm of the user. In such implementations where the blood pressure device 180 is a sphygmomanometer, the blood pressure device 180 also includes a pump (e.g., a manually operated bulb) for inflating the cuff. In some implementations, the blood pressure device 180 is coupled to the respiratory therapy device 122 of the respiratory therapy system 120, which in turn delivers pressurized air to inflate the cuff. More generally, the blood pressure device 180 can be communicatively coupled with, and/or physically integrated in (e.g., within a housing), the control system 110, the memory device 114, the respiratory therapy system 120, the external device 170, and/or the activity tracker 182.

The activity tracker 182 is generally used to aid in generating physiological data for determining an activity measurement associated with the user. The activity measurement can include, for example, a number of steps, a distance traveled, a number of steps climbed, a duration of physical activity, a type of physical activity, an intensity of physical activity, time spent standing, a respiration rate, an average respiration rate, a resting respiration rate, a maximum respiration rate, a respiration rate variability, a heart rate, an average heart rate, a resting heart rate, a maximum heart rate, a heart rate variability, a number of calories burned, blood oxygen saturation, electrodermal activity (also known as skin conductance or galvanic skin response), or any combination thereof. The activity tracker 182 includes one or more of the sensors 130 described herein, such as, for example, the motion sensor 138 (e.g., one or more accelerometers and/or gyroscopes), the PPG sensor 154, and/or the ECG sensor 156.

In some implementations, the activity tracker 182 is a wearable device that can be worn by the user, such as a smartwatch, a wristband, a ring, or a patch. For example, referring to FIG. 2, the activity tracker 182 is worn on a wrist of the user. The activity tracker 182 can also be coupled to or integrated a garment or clothing that is worn by the user. Alternatively, still, the activity tracker 182 can also be coupled to or integrated in (e.g., within the same housing) the external device 170. More generally, the activity tracker 182 can be communicatively coupled with, or physically integrated in (e.g., within a housing), the control system 110, the memory device 114, the respiratory therapy system 120, the external device 170, and/or the blood pressure device 180.

While the control system 110 and the memory device 114 are described and shown in FIG. 1 as being a separate and distinct component of the system 100, in some implementations, the control system 110 and/or the memory device 114 are integrated in the external device 170 and/or the respiratory therapy device 122. Alternatively, in some implementations, the control system 110 or a portion thereof (e.g., the processor 112) can be located in a cloud (e.g., integrated in a server, integrated in an Internet of Things (IoT) device, connected to the cloud, be subject to edge cloud processing, etc.), located in one or more servers (e.g., remote servers, local servers, etc., or any combination thereof.

While system 100 is shown as including all of the components described above, more or fewer components can be included in a system for monitoring the user during one or more sleep sessions to determine whether the user suffers from RBD and/or DEB, according to implementations of the present disclosure. For example, a first alternative system includes the control system 110, the memory device 114, and at least one of the one or more sensors 130. As another example, a second alternative system includes the control system 110, the memory device 114, at least one of the one or more sensors 130, and the external device 170. As yet another example, a third alternative system includes the control system 110, the memory device 114, the respiratory therapy system 120, at least one of the one or more sensors 130, and the external device 170. As a further example, a fourth alternative system includes the control system 110, the memory device 114, the respiratory therapy system 120, at least one of the one or more sensors 130, the external device 170, and the blood pressure device 180 and/or activity tracker 182. Thus, various systems for monitoring the user during one or more sleep sessions to determine whether the user suffers from RBD and/or DEB can be formed using any portion or portions of the components shown and described herein and/or in combination with one or more other components.

As used herein, a sleep session can be defined in a number of ways based at least in part on, for example, an initial start time and an end time. In some implementations, a sleep session is a duration where the user is asleep, that is, the sleep session has a start time and an end time, and during the sleep session, the user does not wake until the end time. That is, any period of the user being awake is not included in a sleep session. From this first definition of sleep session, if the user wakes ups and falls asleep multiple times in the same night, each of the sleep intervals separated by an awake interval is a sleep session.

Alternatively, in some implementations, a sleep session has a start time and an end time, and during the sleep session, the user can wake up, without the sleep session ending, so long as a continuous duration that the user is awake is below an awake duration threshold. The awake duration threshold can be defined as a percentage of a sleep session. The awake duration threshold can be, for example, about twenty percent of the sleep session, about fifteen percent of the sleep session duration, about ten percent of the sleep session duration, about five percent of the sleep session duration, about two percent of the sleep session duration, etc., or any other threshold percentage. In some implementations, the awake duration threshold is defined as a fixed amount of time, such as, for example, about one hour, about thirty minutes, about fifteen minutes, about ten minutes, about five minutes, about two minutes, etc., or any other amount of time.

In some implementations, a sleep session is defined as the entire time between the time in the evening at which the user first entered the bed, and the time the next morning when user last left the bed. Put another way, a sleep session can be defined as a period of time that begins on a first date (e.g., Monday, Jan. 6, 2020) at a first time (e.g., 10:00 PM), that can be referred to as the current evening, when the user first enters a bed with the intention of going to sleep (e.g., not if the user intends to first watch television or play with a smart phone before going to sleep, etc.), and ends on a second date (e.g., Tuesday, Jan. 7, 2020) at a second time (e.g., 7:00 AM), that can be referred to as the next morning, when the user first exits the bed with the intention of not going back to sleep that next morning.

In some implementations, the user can manually define the beginning of a sleep session and/or manually terminate a sleep session. For example, the user can select (e.g., by clicking or tapping) one or more user-selectable element that is displayed on the display device 172 of the external device 170 (FIG. 1) to manually initiate or terminate the sleep session.

Figure 3:
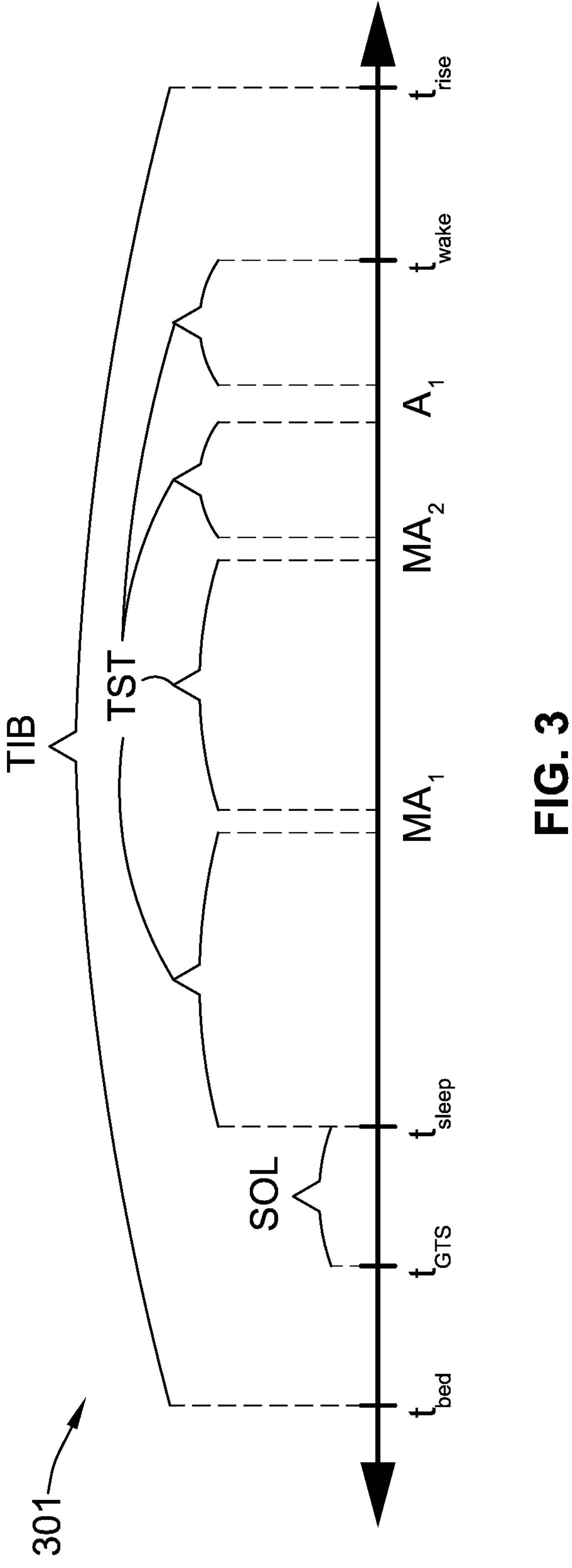
FIG. 3 illustrates an exemplary timeline for a sleep session, according to some implementations of the present disclosure.

Referring to FIG. 3, an exemplary timeline 300 for a sleep session is illustrated. The timeline 300 includes an enter bed time ($t_{bed}$), a go-to-sleep time ($t_{GTS}$), an initial sleep time ($t_{sleep}$), a first micro-awakening $MA_1$, a second micro-awakening $MA_2$, an awakening A, a wake-up time ($t_{wake}$), and a rising time ($t_{rise}$).

The enter bed time $t_{bed}$ is associated with the time that the user initially enters the bed (e.g., bed 230 in FIG. 2) prior to falling asleep (e.g., when the user lies down or sits in the bed). The enter bed time $t_{bed}$ can be identified based at least in part on a bed threshold duration to distinguish between times when the user enters the bed for sleep and when the user enters the bed for other reasons (e.g., to watch TV). For example, the bed threshold duration can be at least about 10 minutes, at least about 20 minutes, at least about 30 minutes, at least about 45 minutes, at least about 1 hour, at least about 2 hours, etc. While the enter bed time $t_{bed}$ is described herein in reference to a bed, more generally, the enter time $t_{bed}$ can refer to the time the user initially enters any location for sleeping (e.g., a couch, a chair, a sleeping bag, etc.).

The go-to-sleep time (GTS) is associated with the time that the user initially attempts to fall asleep after entering the bed ($t_{bed}$). For example, after entering the bed, the user may engage in one or more activities to wind down prior to trying to sleep (e.g., reading, watching TV, listening to music, using the external device 170, etc.). The initial sleep time ($t_{sleep}$) is the time that the user initially falls asleep. For example, the initial sleep time ($t_{sleep}$) can be the time that the user initially enters the first non-REM sleep stage.

The wake-up time $t_{wake}$ is the time associated with the time when the user wakes up without going back to sleep (e.g., as opposed to the user waking up in the middle of the night and going back to sleep). The user may experience one of more unconscious microawakenings (e.g., microawakenings $MA_1$ and $MA_2$) having a short duration (e.g., 5 seconds, 10 seconds, 30 seconds, 1 minute, etc.) after initially falling asleep. In contrast to the wake-up time $t_{wake}$, the user goes back to sleep after each of the microawakenings $MA_1$ and $MA_2$. Similarly, the user may have one or more conscious awakenings (e.g., awakening A) after initially falling asleep (e.g., getting up to go to the bathroom, attending to children or pets, sleep walking, etc.). However, the user goes back to sleep after the awakening A. Thus, the wake-up time $t_{wake}$ can be defined, for example, based at least in part on a wake threshold duration (e.g., the user is awake for at least 15 minutes, at least 20 minutes, at least 30 minutes, at least 1 hour, etc.).

Similarly, the rising time $t_{rise}$ is associated with the time when the user exits the bed and stays out of the bed with the intent to end the sleep session (e.g., as opposed to the user getting up during the night to go to the bathroom, to attend to children or pets, sleep walking, etc.). In other words, the rising time $t_{rise}$ is the time when the user last leaves the bed without returning to the bed until a next sleep session (e.g., the following evening). Thus, the rising time $t_{rise}$ can be defined, for example, based at least in part on a rise threshold duration (e.g., the user has left the bed for at least 15 minutes, at least 20 minutes, at least 30 minutes, at least 1 hour, etc.). The enter bed time $t_{bed}$ time for a second, subsequent sleep session can also be defined based at least in part on a rise threshold duration (e.g., the user has left the bed for at least 4 hours, at least 6 hours, at least 8 hours, at least 12 hours, etc.).

As described above, the user may wake up and get out of bed one more times during the night between the initial $t_{bed}$ and the final $t_{rise}$. In some implementations, the final wake-up time $t_{wake}$ and/or the final rising time $t_{rise}$ that are identified or determined based at least in part on a predetermined threshold duration of time subsequent to an event (e.g., falling asleep or leaving the bed). Such a threshold duration can be customized for the user. For a standard user which goes to bed in the evening, then wakes up and goes out of bed in the morning any period (between the user waking up ($t_{wake}$) or raising up ($t_{rise}$), and the user either going to bed ($t_{bed}$), going to sleep ($t_{GTS}$) or falling asleep ($t_{sleep}$) of between about 12 and about 18 hours can be used. For users that spend longer periods of time in bed, shorter threshold periods may be used (e.g., between about 8 hours and about 14 hours). The threshold period may be initially selected and/or later adjusted based at least in part on the system monitoring the user's sleep behavior.

The total time in bed (TIB) is the duration of time between the time enter bed time $t_{bed}$ the rising time trice. The total sleep time (TST) is associated with the duration between the initial sleep time and the wake-up time, excluding any conscious or unconscious awakenings and/or micro-awakenings therebetween. Generally, the total sleep time (TST) will be shorter than the total time in bed (TIB) (e.g., one minute short, ten minutes shorter, one hour shorter, etc.). For example, referring to the timeline 300 of FIG. 3, the total sleep time (TST) spans between the initial sleep time $t_{sleep}$ and the wake-up time $t_{wake}$, but excludes the duration of the sleep first micro-awakening $MA_1$, the second micro-awakening $MA_2$, and the awakening A. As shown, in this example, the total sleep time (TST) is shorter than the total time in bed (TIB).

In some implementations, the total sleep time (TST) can be defined as a persistent total sleep time (PTST). In such implementations, the persistent total sleep time excludes a predetermined initial portion or period of the first non-REM stage (e.g., light sleep stage). For example, the predetermined initial portion can be between about 30 seconds and about 20 minutes, between about 1 minute and about 10 minutes, between about 3 minutes and about 5 minutes, etc. The persistent total sleep time is a measure of sustained sleep, and smooths the sleep-wake hypnogram. For example, when the user is initially falling asleep, the user may be in the first non-REM stage for a very short time (e.g., about 30 seconds), then back into the wakefulness stage for a short period (e.g., one minute), and then goes back to the first non-REM stage. In this example, the persistent total sleep time excludes the first instance (e.g., about 30 seconds) of the first non-REM stage.

In some implementations, the sleep session is defined as starting at the enter bed time ($t_{bed}$) and ending at the rising time ($t_{rise}$), i.e., the sleep session is defined as the total time in bed (TIB). In some implementations, a sleep session is defined as starting at the initial sleep time ($t_{sleep}$) and ending at the wake-up time ($t_{wake}$). In some implementations, the sleep session is defined as the total sleep time (TST). In some implementations, a sleep session is defined as starting at the go-to-sleep time ($t_{GTS}$) and ending at the wake-up time ($t_{wake}$). In some implementations, a sleep session is defined as starting at the go-to-sleep time ($t_{GTS}$) and ending at the rising time ($t_{rise}$). In some implementations, a sleep session is defined as starting at the enter bed time ($t_{bed}$) and ending at the wake-up time ($t_{wake}$). In some implementations, a sleep session is defined as starting at the initial sleep time ($t_{sleep}$) and ending at the rising time ($t_{rise}$).

Figure 4:
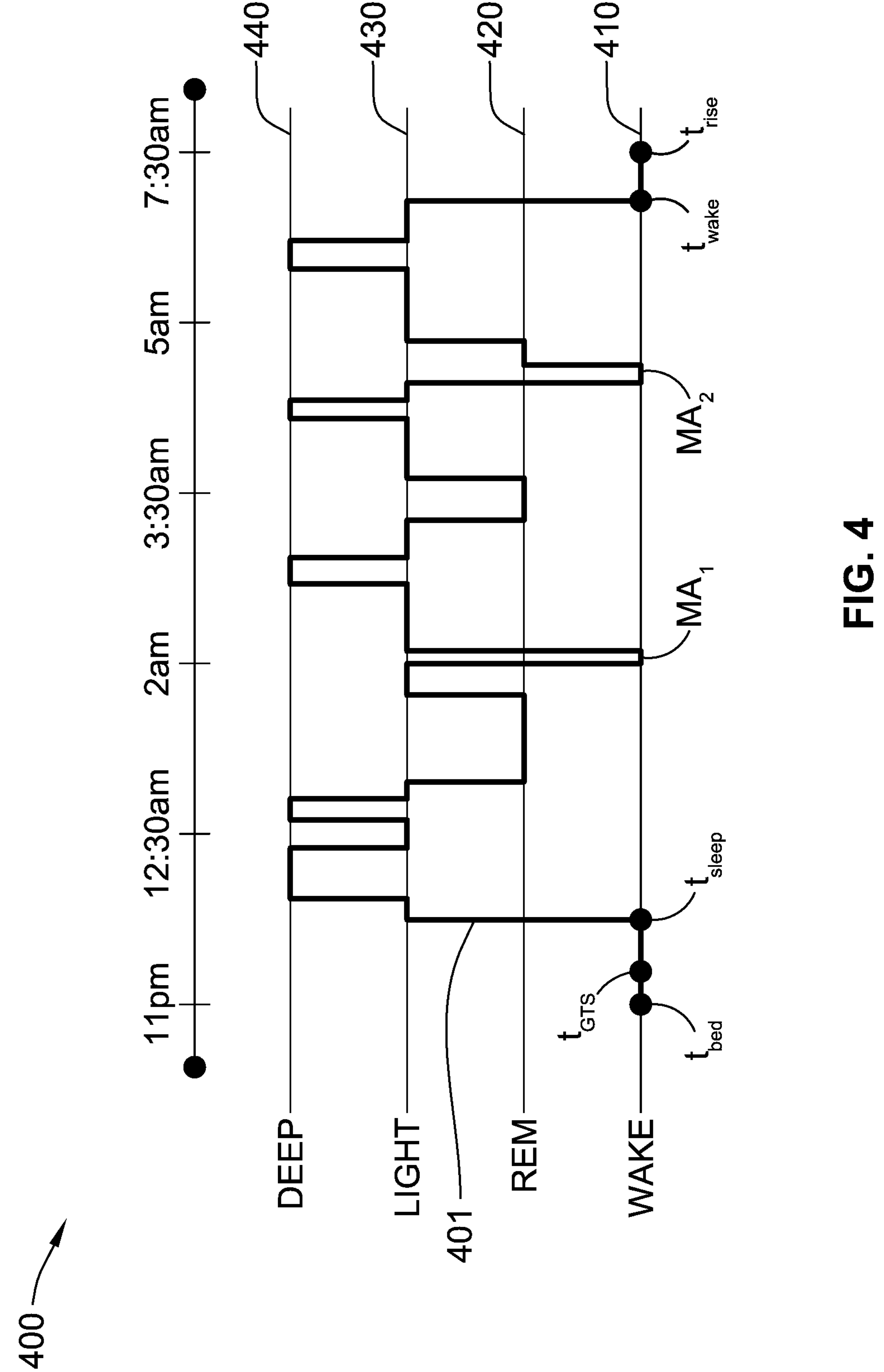
FIG. 4 illustrates an exemplary hypnogram associated with the sleep session of FIG. 3, according to some implementations of the present disclosure.

Referring to FIG. 4, an exemplary hypnogram 400 corresponding to the timeline 300 (FIG. 3), according to some implementations, is illustrated. As shown, the hypnogram 400 includes a sleep-wake signal 401, a wakefulness stage axis 410, a REM stage axis 420, a light sleep stage axis 430, and a deep sleep stage axis 440. The intersection between the sleep-wake signal 401 and one of the axes 410-440 is indicative of the sleep stage at any given time during the sleep session.

The sleep-wake signal 401 can be generated based at least in part on physiological data associated with the user (e.g., generated by one or more of the sensors 130 described herein). The sleep-wake signal can be indicative of one or more sleep stages, including wakefulness, relaxed wakefulness, microawakenings, a REM stage, a first non-REM stage, a second non-REM stage, a third non-REM stage, or any combination thereof. In some implementations, one or more of the first non-REM stage, the second non-REM stage, and the third non-REM stage can be grouped together and categorized as a light sleep stage or a deep sleep stage. For example, the light sleep stage can include the first non-REM stage and the deep sleep stage can include the second non-REM stage and the third non-REM stage. While the hypnogram 400 is shown in FIG. 4 as including the light sleep stage axis 430 and the deep sleep stage axis 440, in some implementations, the hypnogram 400 can include an axis for each of the first non-REM stage, the second non-REM stage, and the third non-REM stage. In other implementations, the sleep-wake signal can also be indicative of a respiration signal, a respiration rate, an inspiration amplitude, an expiration amplitude, an inspiration-expiration amplitude ratio, an inspiration-expiration duration ratio, a number of events per hour, a pattern of events, or any combination thereof. Information describing the sleep-wake signal can be stored in the memory device 114.

The hypnogram 400 can be used to determine one or more sleep-related parameters, such as, for example, a sleep onset latency (SOL), wake-after-sleep onset (WASO), a sleep efficiency (SE), a sleep fragmentation index, sleep blocks, or any combination thereof.

The sleep onset latency (SOL) is defined as the time between the go-to-sleep time ($t_{GTS}$) and the initial sleep time ($t_{sleep}$). In other words, the sleep onset latency is indicative of the time that it took the user to actually fall asleep after initially attempting to fall asleep. In some implementations, the sleep onset latency is defined as a persistent sleep onset latency (PSOL). The persistent sleep onset latency differs from the sleep onset latency in that the persistent sleep onset latency is defined as the duration time between the go-to-sleep time and a predetermined amount of sustained sleep. In some implementations, the predetermined amount of sustained sleep can include, for example, at least 10 minutes of sleep within the second non-REM stage, the third non-REM stage, and/or the REM stage with no more than 2 minutes of wakefulness, the first non-REM stage, and/or movement therebetween. In other words, the persistent sleep onset latency requires up to, for example, 8 minutes of sustained sleep within the second non-REM stage, the third non-REM stage, and/or the REM stage. In other implementations, the predetermined amount of sustained sleep can include at least 10 minutes of sleep within the first non-REM stage, the second non-REM stage, the third non-REM stage, and/or the REM stage subsequent to the initial sleep time. In such implementations, the predetermined amount of sustained sleep can exclude any micro-awakenings (e.g., a ten second micro-awakening does not restart the 10-minute period).

The wake-after-sleep onset (WASO) is associated with the total duration of time that the user is awake between the initial sleep time and the wake-up time. Thus, the wake-after-sleep onset includes short and micro-awakenings during the sleep session (e.g., the micro-awakenings $MA_1$ and $MA_2$ shown in FIG. 4), whether conscious or unconscious. In some implementations, the wake-after-sleep onset (WASO) is defined as a persistent wake-after-sleep onset (PWASO) that only includes the total durations of awakenings having a predetermined length (e.g., greater than 10 seconds, greater than 30 seconds, greater than 60 seconds, greater than about 5 minutes, greater than about 10 minutes, etc.)

The sleep efficiency (SE) is determined as a ratio of the total time in bed (TIB) and the total sleep time (TST). For example, if the total time in bed is 8 hours and the total sleep time is 7.5 hours, the sleep efficiency for that sleep session is 93.75%. The sleep efficiency is indicative of the sleep hygiene of the user. For example, if the user enters the bed and spends time engaged in other activities (e.g., watching TV) before sleep, the sleep efficiency will be reduced (e.g., the user is penalized). In some implementations, the sleep efficiency (SE) can be calculated based at least in part on the total time in bed (TIB) and the total time that the user is attempting to sleep. In such implementations, the total time that the user is attempting to sleep is defined as the duration between the go-to-sleep (GTS) time and the rising time described herein. For example, if the total sleep time is 8 hours (e.g., between 11 PM and 7 AM), the go-to-sleep time is 10:45 PM, and the rising time is 7:15 AM, in such implementations, the sleep efficiency parameter is calculated as about 94%.

The fragmentation index is determined based at least in part on the number of awakenings during the sleep session. For example, if the user had two micro-awakenings (e.g., micro-awakening $MA_1$ and micro-awakening $MA_2$ shown in FIG. 4), the fragmentation index can be expressed as 2. In some implementations, the fragmentation index is scaled between a predetermined range of integers (e.g., between 0 and 10).

The sleep blocks are associated with a transition between any stage of sleep (e.g., the first non-REM stage, the second non-REM stage, the third non-REM stage, and/or the REM) and the wakefulness stage. The sleep blocks can be calculated at a resolution of, for example, 30 seconds.

In some implementations, the systems and methods described herein can include generating or analyzing a hypnogram including a sleep-wake signal to determine or identify the enter bed time ($t_{bed}$), the go-to-sleep time ($t_{GTS}$), the initial sleep time ($t_{sleep}$), one or more first micro-awakenings (e.g., $MA_1$ and $MA_2$), the wake-up time ($t_{wake}$), the rising time ($t_{rise}$), or any combination thereof based at least in part on the sleep-wake signal of a hypnogram. The hypnogram can be generated in real-time during the sleep session, or can be generated after the sleep session is completed.

In other implementations, one or more of the sensors 130 can be used to determine or identify the enter bed time ($t_{bed}$), the go-to-sleep time ($t_{GTS}$), the initial sleep time ($t_{sleep}$), one or more first micro-awakenings (e.g., $MA_1$ and $MA_2$), the wake-up time ($t_{wake}$), the rising time ($t_{rise}$), or any combination thereof, which in turn define the sleep session. For example, the enter bed time $t_{bed}$ can be determined based at least in part on, for example, data generated by the motion sensor 138, the microphone 140, the camera 150, or any combination thereof. The go-to-sleep time can be determined based at least in part on, for example, data from the motion sensor 138 (e.g., data indicative of no movement by the user), data from the camera 150 (e.g., data indicative of no movement by the user and/or that the user has turned off the lights), data from the microphone 140 (e.g., data indicative of the using turning off a TV), data from the external device 170 (e.g., data indicative of the user no longer using the external device 170), data from the pressure sensor 132 and/or the flow rate sensor 134 (e.g., data indicative of the user turning on the respiratory therapy device 122, data indicative of the user donning the user interface 124, etc.), or any combination thereof.

Figure 5:
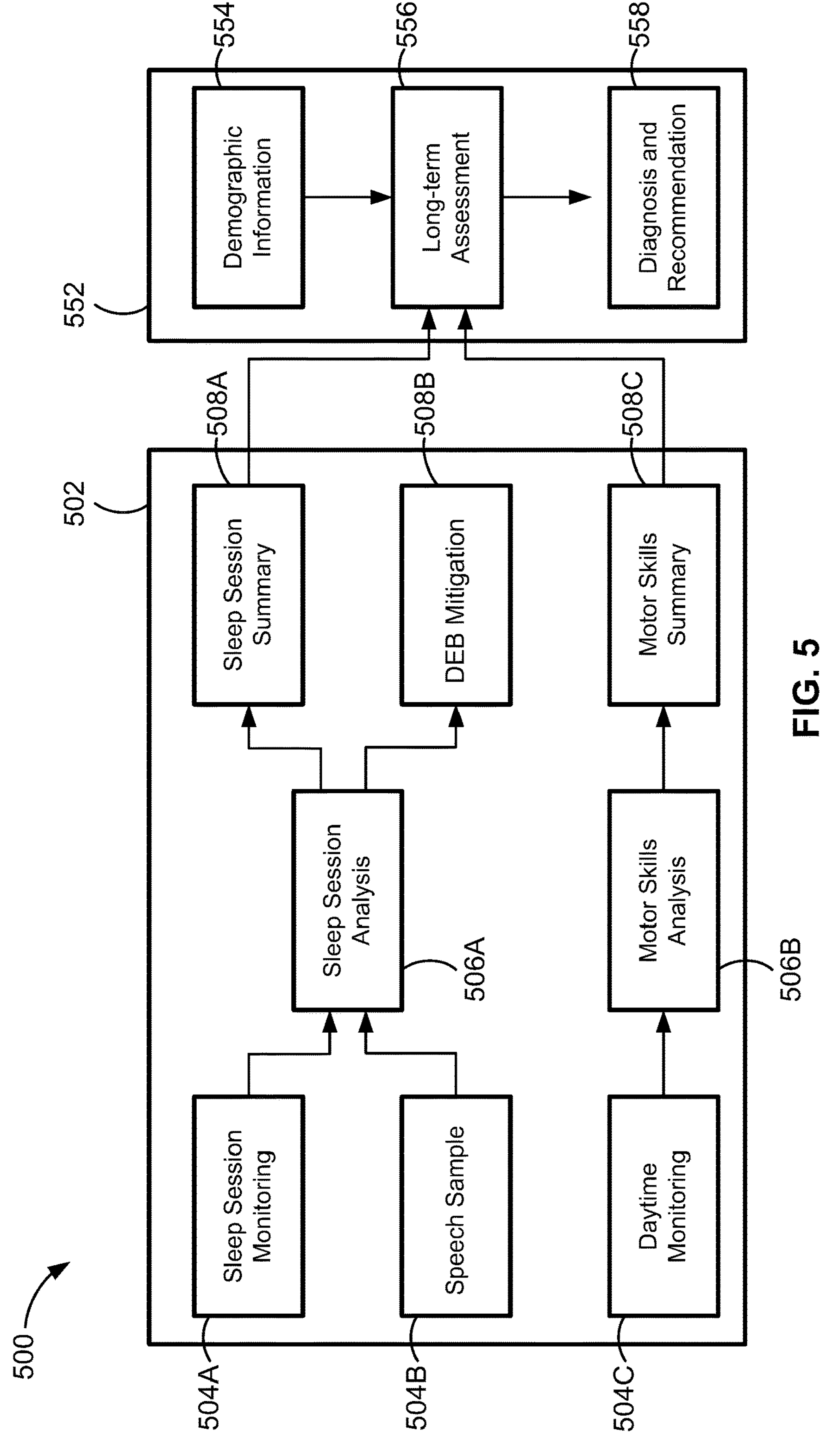
FIG. 5 is a functional block diagram of a first algorithm for monitoring a sleep session, according to some implementations of the present disclosure.

FIG. 5 illustrates a block diagram of an example algorithm 500 for monitoring a user (such as user 210) and determining whether the user 210 has RBD and/or DEB. The algorithm 500 generally includes two separate components 502 and 552. Component 502 is used for daily and nightly monitoring of the user, while component 552 can used for long term assessment and diagnosis. In one implementation, component 502 is implemented a personal device of the user (such as external device 170). Thus, in some implementations, component 502 is implemented as a program or application on the user's mobile device (e.g., phone, tablet, laptop, etc.). Component 552 can also be implemented on a personal device of the user, but in many implementations is implemented as part of a cloud-based platform. This allows the longer term assessment and diagnosis information to be accessed by third-parties, such as the user's healthcare provider, caretaker, friend, family member, etc. In other implementations, components 502 and 552 can be implemented on any combination of devices, platforms, etc. Generally, components 502 and 552 can be implemented as part of the system 100 (FIG. 1).

Component 502 includes both a night-time monitoring portion (shown in the upper and middle blocks of component 502), and a day-time monitoring portion (shown in the lower blocks of component 502). Blocks 504A and 504B are inputs to the night-time monitoring portion of component 502. At block 504A, the user is monitored during the sleep session to detect any atypical REM sleep stages and/or DEB. The sleep session monitoring of block 504A generally includes tracking the user's movement and vocalizations (e.g., speech and non-speech) during the sleep session, for example using any of sensors 130 (FIG. 1). Movement can be tracked using a variety of different movement sensors that generate movement data. Vocalizations that the user makes during the sleep session (such as speech, muttering, crying, snoring, coughing, choking, etc.) can be tracked using audio sensors that generate audio data. Other types of data can also be used. For example, respiration data related to the user's respiration can be generated (together with the motion data referred to as biomotion data). Optical data related to the light levels in the user's surroundings (e.g., in the user's bedroom) can be generated. And temporal data related to a time elapsed within the sleep session can be generated. Generally, the data is obtained from non-invasive means, such as by using movement sensors, audio sensors, and the like. More invasive sensors such as EEG sensors, ECG sensors, or EOG sensors do not need to be used.

At block 504B, audio samples from the user are generated. The audio samples are known to be of the user making various vocalizations (including speech, and non-speech such as coughing, grunting, snoring, crying, etc.), and can aid in determining whether the vocalizations detected during the sleep session were actually produced by the user (as opposed to the user's bed partner), and if so, whether the vocalizations are speech or non-speech. In some implementations, the user is recorded during the day to generate the known audio samples. In other implementations, the user is prompted to speak certain phrases, which are recorded. The recording can be done using the user's mobile device (e.g., phone, tablet), or any other suitable device. For example, in some implementations, a smart speaker in the user's bedroom can record audio samples from the user before the user begins a sleep session (e.g., before the user gets into bed at night), or after the user ends a sleep session (e.g., after the user gets out of bed in the morning).

The data from block 504A and the audio samples from block 504B are used to analyze the sleep session at block 506A. Generally, the analysis performed at block 506A can be implemented using one or more algorithms. These algorithms can be machine learning algorithms that have been trained to identify different sleep stages the user goes through during the sleep session, based at least on the data from night-time monitoring block 504A and the data from the audio sample block 504B. Modules of the algorithm 500 can be pre-trained on data from clinical references (data recorded in sleep laboratories, data identifying sleep stages, RBD and DEB episodes scored by experts, etc.). The pre-training can provide a good baseline performance when applied on new users (data the algorithm 500 has not seen before). Automatic retraining of the algorithm 500 with user-specific data can occur once the algorithm 500 is deployed. This training can optimize the performance of the algorithm 500 for the specific user. In some implementations, separate trained algorithms are used to determine the various sleep stages and to detect whether the user is undergoing DEB. In other implementations, a single trained algorithm can determine the various sleep stages and detect whether the user is undergoing DEB. Thus, the sleep session analysis at block 506A can when the user is experiencing an atypical REM sleep stage indicative of RBD, and also whether the user experiences DEB during any of the atypical REM sleep stages. The sleep session analysis at block 506A can occur in real-time during the sleep session, based on the data from the sleep session monitoring of block 504A.

The sleep session analysis at block 506A generally has two different outputs at blocks 508A and 508B. At block 508A, sleep session summary data is generated. The sleep session summary includes details on the number of different sleep stages the user experienced during the sleep session, as well as the time spent in each different sleep stage during the sleep session. Thus, the sleep session analysis indicates to the user and/or third-parties a total number of atypical REM sleep stages experienced by the user during the sleep session, and also the total amount of time spent in atypical REM sleep stages during the sleep session. In some implementations, the sleep session summary is produced as a hypnogram, which shows a timeline of the user's sleep session and the various sleep stages the user experienced throughout the sleep session. In some implementations, the sleep session summary is generated at the end of the sleep session. In other implementations, the sleep session summary can be generated in real-time during the sleep session, which may be useful if a third part if monitoring the user's sleep session.

The other output of the sleep session analysis block 506A is block 508B, where DEB mitigation occurs. If the real-time sleep session analysis of block 506A determines that the user is currently undergoing DEB, the system 100 can activate the DEB mitigation system 184 to reduce or end the user's DEB, or lessen the impact the DEB has on the user or the user's bed partner. As discussed herein, DEB mitigation can be accomplished in several ways, such as using an audible alarm, a light, a bed adjustment mechanism to move or vibrate the user's bed, a physical contact mechanism to make contact with the user, or a guard or barrier to mitigate any harm the DEB might cause to the user or the user's bed partner.

Component 502 also includes daytime monitoring at block 504C. Generally, the daytime monitoring includes monitoring the user's movement during the day. A variety of different motor abnormalities can be correlated with neuro-degenerative disorders (including RBD), such as rigidity, gait abnormalities, limb bradykinesia, tremors, and others. A variety of different devices can be used to track the user's movement and generate movement data, such as a pedometer, a smart watch, a wearable fitness device, a mobile device (such as external device 170). At block 506B, the movement data is used to perform a motor skills analysis. The movement data can be analyzed to determine various characteristics related to the user's postural sway, gait, and limb movement. Aspects of the user's gait can include jerking, harmonic stability, and oscillation range. Aspects of the user's limb movement can include arm swing, or asymmetry between left and right arms or left and right legs.

The output of the motor skills analysis at block 506B is a motor skills summary at block 508C. In some implementations, summary charts can be generated for the user to view. In other implementations, the motor skills summary data is used as part of a long-term assessment.

The data from the sleep session summary of block 508A and the motor skills summary of block 508C can be used as part of the long term assessment and diagnosis performed by component 552. Generally, the sleep session summary data for every sleep session is an input to the long-term assessment performed at block 556 of component 552, e.g., every morning after the user wakes up and the sleep session ends, a new set of sleep session summary data provided to block 556. Motor skills summary data from block 508C can also be periodically inputted to block 556.

Block 556 can also incorporate demographic information that is provided at block 554. The demographic information can be demographic information related to the user, such as age, gender, sex, ethnicity, medical history, etc. However, the demographic information can also include demographic information from other users as well. In these implementations, the demographic information generally also includes information related to whether those users have RBD, and can include sleep session data, motion data, and speech data about those other users. This enables RBD and/or DEB to be correlated with certain demographic factors, and also allows for the comparison of the user's data to data from other users in the same population.

The output of the long-term assessment is a diagnosis and recommendation at block 558. Block 558 generally provides an assessment of the user's long-term prognosis. The user's long-term prognosis can show potential development of RBD over time, based on data from multiple sleep session and based on movement data from long time periods. Generally, RBD is a slowly-developing disorder, and thus the diagnosis at block 558 can include a risk factor or severity score, for example if the user is in the early stages of RBD. The risk factor could also indicate the user's risk of developing other types of neuro-degenerative disorders as well. The recommendation can include suggestions for treatment options (e.g., medicine), suggestions for mitigating or ending DEB the user experiences during the sleep session, recommendations to follow up with the user's healthcare provider, or other pertinent suggestions or recommendations.

In some implementations, the audio samples of block 504B are also used directly in the long-term assessment of block 556. There are a variety of vocal abnormalities that can be analyzed together with, or apart from, vocalizations occurring during sleep sessions and which can also be early indicators of neuro-degenerative disorders such as RBD. These abnormalities can be related to sustained phonation, such as pitch fluctuation, noise, or aperiodicity during sustained phonation. The abnormalities may also be related to articulation, such as imprecise vowels and consonants, slow and irregular syllables, and articulatory decay. In a further example, the abnormalities can be related to prosody, and can include reduce loudness, reduced loudness variation, reduced pitch variation, and inappropriate silences. Long-term tracking of the user's vocalizations enables identification of these abnormalities, which aids in early diagnosis of RBD.

Figure 6:
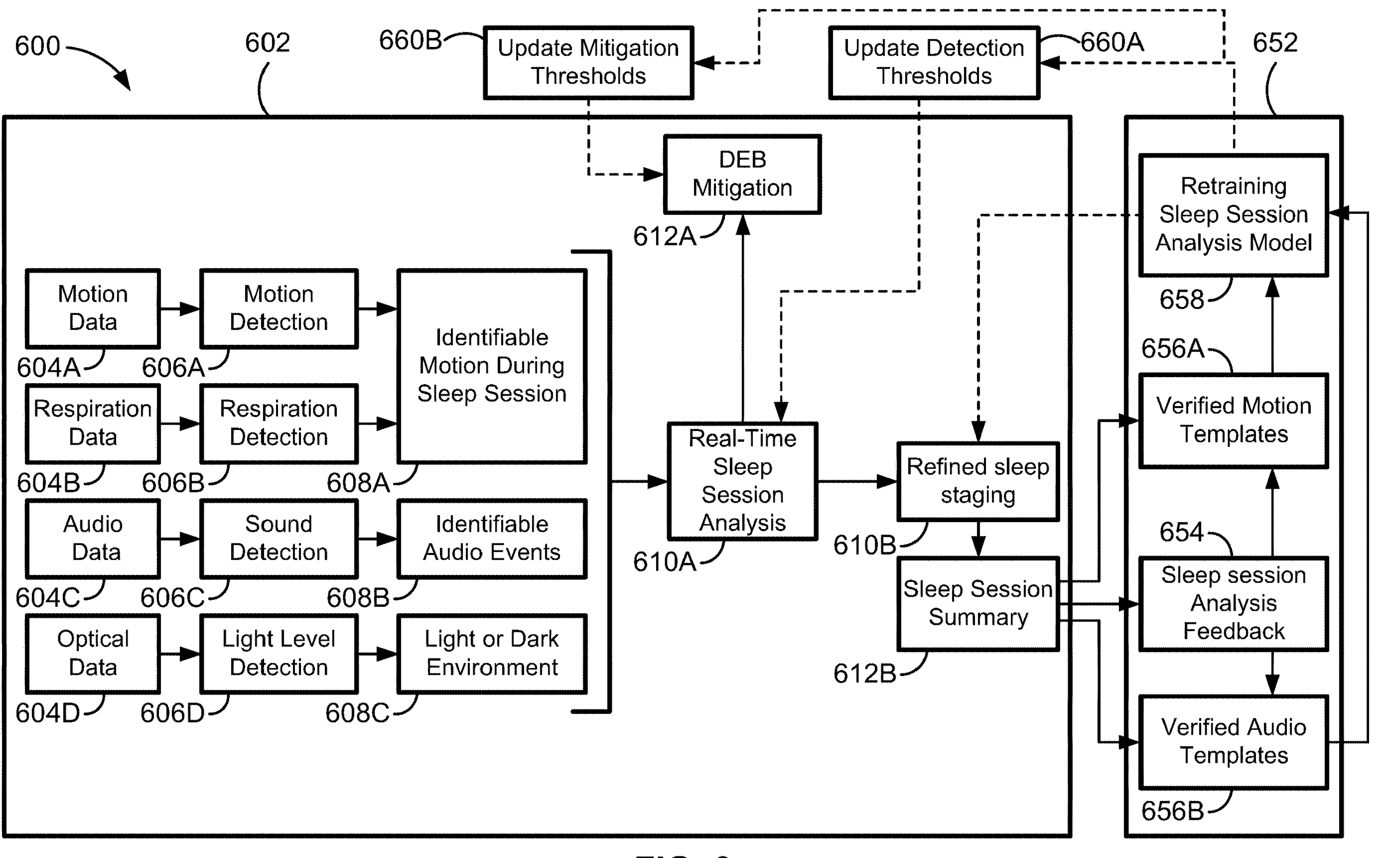
FIG. 6 is a functional block diagram of a second algorithm for monitoring a sleep session, according to some implementations of the present disclosure.

Referring now to FIG. 6, an example algorithm 600 for monitoring a sleep session is illustrated. Generally, algorithm 600 is a more detailed illustration of the nighttime monitoring portion of component 502 of algorithm 500. Algorithm 600 includes model component 602, and a retraining component 652. The inputs to the model component 602 of algorithm 600 can include motion data at block 604A, respiration data at block 604B, audio data at block 604C, and optical data at block 604D. All of these data can be generated, in some implementations, by any one or more of the sensors 130 of the system 100. The motion data at block 604A can be generated by the motion sensor 138, which can include accelerometers, gyroscopes, magnetometers, etc. The respiration data at block 604B can be generated by the pressure sensor 132, the flow rate sensor 134, the motion sensor 138, the microphone 140, or any combination thereof. The audio data at block 604C can be generated by the microphone 140. The optical data at block 604D can be generated by the camera 150 or the IR sensor 152. Any of the data at blocks 604A-604D can be generated by other sensors as well.

The motion data 604A is analyzed at block 606A to detect motion made by the user during the sleep session, including limb movement. The motion detection at block 606A may also identify other motion, such as motion of the user's bed partner. The respiration data at block 604B is analyzed at block 606B to detect the respiration of the user. The audio data at block 604C is analyzed at block 606C to detect vocalizations produced during the sleep session, which can include speech and non-speech of the user, speech and non-speech of the user's bed partner, and any other detected audio. In some implementations, the audio data at block 604C is analyzed using machine learning algorithms such as a recurrent neural network to extract specific events. Finally, optical data at block 604D can be analyzed at block 606D to determine a light level in the area where the user is located during the sleep session, e.g., the user's bedroom.

At block 608A, the detected motion at block 606A and the detected respiration at block 606B are used to flag identifiable motion events during the sleep session. This can include specific motion patterns of the user's limbs such as punches, kicks, etc.; as well as various attributes of the motion such as speed, acceleration, etc. The identifiable motion can also relate to the user's respiration, such as respiration rate and respiration amplitude. In some implementations, block 608A can also utilize the detected sound from block 606C and the detected light level from block 606D.

At block 608B, specific audio events are flagged as being relevant. For example, if the algorithm 600 determines that certain audio events identified during the vocalization detection at block 604C were produced by the user's bed partner, those audio events can be discarded. Identified audio events determined to be from the user can be retained for further use. The identified audio events can include any vocalizations of interest, such as speech, crying, muttering, choking, coughing, etc. In particular, speech with recognizable pitch, intensity, and verbal content can be flagged, as these types of events often occur in a user with RBD. In some implementations, block 608B can also utilize the detected motion from block 606A, the detected respiration from block 606B, and the detected light level from block 606D.

At block 608C, the area in which the user is at during the sleep session is identified as a light or dark environment. Based on the light levels in the area (e.g., the user's bedroom), block 608C determines whether it is light or dark, which in turn can be used in determining whether the user is experiencing an atypical REM sleep stage. In some implementations, block 608C can also utilize the detected motion from block 606A, the detected respiration from block 606B, and the detected sound from block 606C.

The identifiable motion of block 608A, the identifiable audio events of block 608B, and the determined lightness or darkness of the user's environment of block 608C can also be used as inputs at block 610A, which performs a real-time sleep session analysis. The real-time sleep session analysis identifies various sleep stages of the sleep session as those sleep stages occur.

One of the outputs of the real-time sleep session analysis is detected occurrences of DEB. When DEB is detected, real-time DEB mitigation at block 612A can occur. As discussed herein, DEB mitigation can occur in a variety of ways, including using an audible alarm, a light, a bed adjustment mechanism to move or vibrate the user's bed, a physical contact mechanism to make contact with the user, or a guard or barrier to mitigate any harm the DEB might cause to the user or the user's bed partner.

The results of the real-time sleep session analysis at block 610A are also used as an input to block 610B, which generally performs a more refined sleep analysis after the sleep session has ended. Generally, the refined sleep analysis of block 610B is performed by one or more trained algorithms or models. The sleep session analysis at block 610B can thus utilize more data in identifying various sleep stages of the sleep session. The output of the sleep session analysis of block 610B is a sleep session summary at block 612B. The sleep session summary identifies all of the sleep stages the user experienced during the sleep session, and how long each sleep stage lasted. In some implementations, the sleep session summary is in the form of a hypnogram, as further described herein.

In the retraining component 652, the trained algorithms/models that perform the real-time sleep session analysis at block 610A and the refined sleep session analysis at block 610B can be updated. At block 654, feedback on the sleep session analysis can be provided. In some examples, the user provides feedback about the sleep session summary, which can include confirming various sleep stages, start and end times of the sleep session, the occurrence of DEB, or other aspects of the sleep session summary. Based on the sleep session summary of block 612B and the feedback of block 654, verified templates can be created or updated. A verified motion template is generated at block 656A, and includes data indicative of specific movements of the user that tend to reoccur during sleep sessions. The verified motion template generated at block 656A can also generally include any type of confirmed data or information related to movement that can be used to updated the trained algorithms of blocks 610A and 610B. Similarly, a verified audio template is generated at block 656B, and includes data indicative of vocalization (e.g., speech or non-speech) confirmed to be made by the user, or generally any type of confirmed data or information related to audio that can be used to updated the trained algorithms of blocks 610A and 610B. Both of these templates can be used as inputs to retraining block 658, where the trained models can be retrained, for example with user-specific information. The refined sleep session analysis can thus be made more accurate for future sleep sessions.

At block 660A, updated detection thresholds for the real-time sleep session analysis of block 610A are created. The detection thresholds generally tell the trained algorithm what types of data indicate the various sleep stages, and when DEB is occurring. At block 660B, updated mitigation thresholds for the DEB mitigation of block 612A are created. The mitigation thresholds generally indicate when some type of DEB mitigation should be performed. For example, some DEB may occur that is not severe enough to require any mitigation. By updating the mitigation thresholds at block 660B, algorithm 600 can more accurately determine when the severity of the DEB is sufficient to warrant mitigation. The thresholds generated at block 660A and 660B can be generated by any suitable mechanism, including updating various the various algorithms and models with new user-specific data, new data of people similar to the user (e.g., people in the same demographic population of the user), or any other data.

Figure 7C:
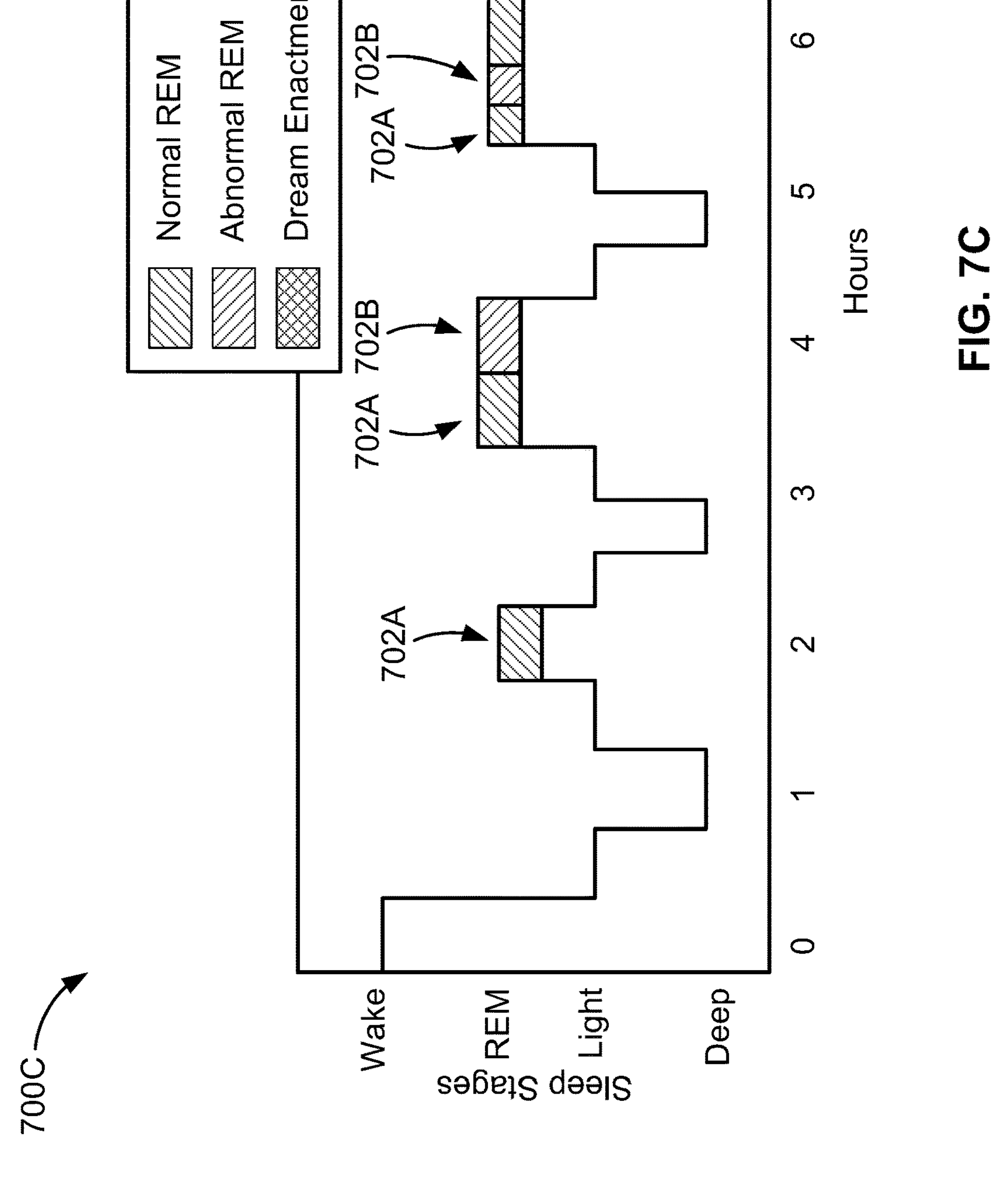
FIG. 7C is a hypnogram of a user experiencing typical rapid eye movement sleep stages, atypical rapid eye movement sleep stages, and dream enactment behavior during a sleep session, according to some implementations of the present disclosure.

FIGS. 7A, 7B, and 7C show different hypnograms that can be created for users with varying levels of RBD. Each of the hypnograms shows four different sleep cycles. FIG. 7A shows hypnogram 700A of a sleep session for a user with no RBD. As can be seen, the REM sleep stage for each sleep cycle is a typical REM sleep stage 702A. Hypnogram 700B in FIG. 7B shows the summary of a sleep session for a user with mild to moderate RBD. As is shown, the REM sleep stage of the first cycle is a typical REM sleep stage 702A. However, the user begins to experience atypical REM sleep stages during later sleep cycles. The REM sleep stages of the second sleep cycle and the third sleep cycle include both typical REM sleep stages 702A and atypical REM sleep stages 702B. Finally, hypnogram 700C in FIG. 7C shows the summary of a sleep session for a user with RBD who has begun to exhibit DEB. In the first sleep cycle, the REM sleep stage includes only a typical REM sleep stage 702A. In the second sleep cycle and the third sleep cycle, the REM sleep stage consists of both a typical REM sleep stage 702A and an atypical REM sleep stage 702B, similar to hypnogram 700B in FIG. 7B. In the fourth sleep cycle, the user experiences DEB, and thus the REM sleep stage of the fourth sleep cycle is comprised of only a DEB stage 702C.

Figure 8:
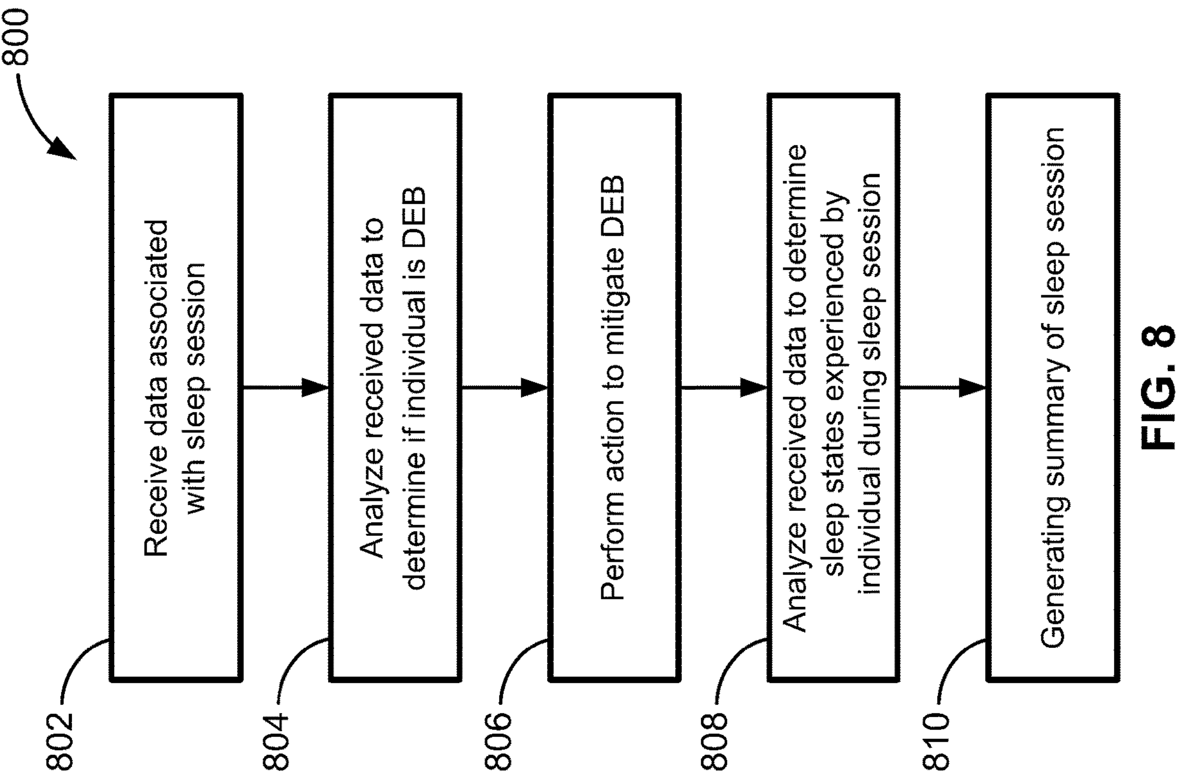
FIG. 8 is a process flow diagram for a first method of monitoring a sleep session, according to some implementations of the present disclosure.

Referring to FIG. 8, a method 800 for monitoring a sleep session is illustrated. Generally, a control system (such as the control system 110 of the system 100) or a portion of the control system such as a processor (such as the one or more processors 112) is configured to carry out the various steps of method 800 (or other methods disclosed herein). A memory device (such as the memory device 114 of the system 100) can be used to store any type of data utilized in the steps of method 800 (or other methods). Method 800 is a specific implementation of example algorithms 500 and 600, which can be used with a variety of different methods.

Step 802 of method 800 includes receiving data associated with the sleep session of the user. The received data can include a variety of different types of data, such as respiration data, motion data indicative of motion of the individual during the sleep session, audio data indicative of vocalizations detected during the sleep session, optical data indicative of light in an area where the individual is located during the sleep session, or any combination thereof. The data can also include temporal data indicative of a time elapsed during the sleep session. The data can be generated, for example, using any one or more of sensors 130.

Step 804 of method 800 includes analyzing the received data to determine if the user is experiencing DEB during the sleep session. In some implementations, machine learning tools (such as a trained DEB algorithm) are used to determine if the user is experiencing DEB. The trained DEB algorithm is configured to make a variety of determinations, including whether sound detected during the sleep session are vocalizations made by the user or the user's bed partner, and whether vocalizations made by the user are speech or non-speech. In some implementations, the DEB algorithm analyzes additional audio data of the user speaking outside of a sleep session to aid in determining whether detected vocalizations during the sleep session are speech made by the user. In still further implementations, the DEB algorithm determines whether the detected sound is from a separate source, such as an electronic device in the user's room. The DEB algorithm can also analyze the motion data, the respiration data, and the optical data to aid in determining whether the user is experiencing DEB. The DEB algorithm could also identify verbal content in any detected vocalizations. Based on the identified verbal content, the system 100 can identify emotions of the user such as fear or terror, which can be indicative of DEB. Generally, a minimum amount of data must be received in order to analyze the data and determine if the user is experiencing DEB. In some implementations, the minimum amount of received data is data generated during a 30-second time period within the sleep session. In other implementations, the minimum amount of received data is data generated during a two-minute time period within the sleep session.

Step 806 of method 800 includes performing an action to mitigate the user's DEB. This action can include activating a light source, activating an audible alarm, causing the bed on which the user is lying to move, causing the individual to physically move, taking steps to prevent the user or the user's bed partner to be harmed, or any combination thereof. In some implementations, the action is configured to aid in ending the user's DEB, by waking the user up or causing them to exit the atypical REM sleep stage. In other implementations, the action is configured to mitigate the severity of the DEB itself, such as by impeding movement of the user and/or the user's limbs, or by protecting the user and/or the user's bed partner. Generally, steps 804 and steps 808 are continually performed in real-time during the sleep session to ensure that whenever the user experiences DEB, the DEB can be detected and mitigated.

At step 808, the received data is analyzed to determine the various different sleep stages experienced by the individual during the sleep session. These sleep stages can include a light sleep stage, a deep sleep stage, a typical REM sleep stage, an atypical REM sleep stage, and a wake state. In contrast to steps 804 and 806, step 808 can be performed at any point during or after the sleep session. If performed during the sleep session, the data can be continually analyzed to determine the various sleep stages the user experiences. However, because merely experiencing an atypical REM sleep stage does not require real-time intervention (in contrast to experiencing DEB, which does not occur during every atypical REM sleep stage), the data can be analyzed following the sleep session to determine the different sleep stages the user experienced during the sleep session. In some implementations, trained machine learning algorithms are used to analyze the data and determine the various different sleep stages the user experienced during the sleep session. These trained algorithms can be the same or different from the trained DEB algorithm used to determine in real-time whether the user is experiencing DEB.

In some implementations, the different types of data are looked at individually to determine what sleep stage the user is in. For example, detecting movement above a certain threshold can indicate that the user is undergoing the deliberate and complex movement common to atypical REM sleep stages and/or DEB, such as pointing, kicking, punching, etc. In another example, detecting that vocalizations produced during the sleep session are made by the user can indicate that the user is in an atypical REM sleep stage or is experiencing DEB. In yet a further example, the optical data can be analyzed to determine the light levels in the area where the sleep session is occurring, which is normally the user's bedroom. Light levels above a certain threshold can aid in determining that the user is in a wake state, while light levels below the threshold can aid in determining that the user is in some type of sleep stage, such as light, deep, typical REM, or atypical REM.

Different types of data can be combined to reveal insights about the user's sleep session, such as whether the user is experiencing an atypical REM sleep stage and/or experiencing DEB. In particular, because detecting movement can occur in both wake state and atypical REM sleep stages, it is useful to cross-check motion data with other data to determine if the user is truly in an atypical REM sleep stage, or is simply awake and moving around. In one example, temporal data and motion data are combined. The temporal data can be analyzed to determine a time elapsed during the sleep session, for example by using a timer from the start of the sleep session, or by comparing the current time to the time the sleep session begin. The motion data is analyzed to determine if the user is moving. Generally, REM sleep stages occur later during the sleep session, generally in the second half. Thus, motion occurring after a first amount of time has elapsed (which can be, for example, a maximum of 4 hours) indicates that the motion is because the user is in a wake state, while motion occurring when a second amount of time has elapsed (which can be, for example, a minimum of 4 hours) indicates that the motion is because the user is currently in an atypical REM sleep stage. Temporal data can also be combined with audio data. If the audio data reveals that the user is speaking after the first amount of time has elapsed, the system 100 can generally determine that the speech is because the user is in a wake state. If the audio data reveals that the user is speaking when the second amount of time has elapsed, the system 100 can determine that the speech is because the user is in an atypical REM sleep stage or is experiencing DEB. In still other implementations, the time elapsed can be combined with knowledge of sleep stages already experienced by the user during the sleep session. Generally, if it is determined that the user has already experienced certain prior sleep stages at a certain elapsed time within the sleep session, the system 100 can determine what sleep stage the user is currently in, or the percentage chance that the current sleep stage is a specific one of the sleep stages.

In another example, motion data is combined with respiration data. The respiration data is analyzed to determine a respiration rate variability rate. Generally, the respiration rate variability of the user is high during both typical and atypical REM sleep stages. Determining that the user has a respiration rate variability above a threshold while motion is occurring indicates that the user is experiencing DEB or is in an atypical REM sleep stage. Determining that the user has a respiration rate variability above the same threshold but while no motion is occurring indicates that the user is in a typical REM sleep stage. The respiration rate can also be used instead of the respiration rate variability. In a further example, the motion data is combined with the optical data, which is analyzed to determine the light level in the area where the user is during the sleep session. Detecting movement when the light level is above a certain threshold (e.g., the bedroom lights or a lamp are on) indicates that the user is awake. In contrast, detecting movement when the light level is below the threshold (e.g., the lights are off) indicates that the user is not awake, and that the detected movement is because the user is in an atypical REM sleep stage, or is experiencing DEB. In yet another example, the same light level analysis can be combined with vocalizations detected during the sleep session. Detecting that the user is speaking when the light levels are below the threshold can indicate that the user is in an atypical REM sleep stage or is experiencing DEB. Detecting that the user is speaking when light levels are above the threshold can indicate that the user is in the wake state.

Other data can also be used to determine to aid in determining which sleep stage the user is in. In some implementations, the system 100 has access to the user's medical history. Data from the medical history may reveal certain conditions or diseases the user has that can provide additional insight into the sleep session. For example, the medical history may indicate that the user has been treated for or diagnosed with RBD in the past, which may indicate that detected motion or vocalizations are more likely due to the user being in an atypical REM sleep stage. In another example, the user's medical history may provide other reasons as to why the user may be moving or speaking during the sleep session, which can indicate that the user is not in an atypical REM sleep stage, despite detecting movement and/or vocalizations during the sleep session. The user can also be provided with a questionnaire that can reveal information that may be helpful in determining which sleep stage the user is in. For example, if the user indicates on the questionnaire that they have a condition such as insomnia or periodic limb movement (PLM), the trained algorithms can more accurately determine whether movement is due to the user being in an atypical REM sleep stage, or due to the user's insomnia or periodic limb movement. Furthermore, the algorithm can contain additional modules that are able to determine potential other conditions or sleep disorders, such as based on the respiration signal, detected vocalizations, or movement. In one example, PLM can be detected based on the periodicity of movement patterns. In another example, OSA can be detected based on a respiration signal and detected snoring. These modules can thus eliminate confounding factors in detection of atypical REM and/or DEB.

The other data could also be historical data associated with one or more prior sleep sessions. The system 100 can analyze the historical data to determine if similar aspects are present in the data from the current sleep session. If the historical data correlates any feature, trend, etc. with a particular sleep stage, the system 100 can use these correlations to aid in determining when similar features or trends from the current sleep session indicate that the user is in a particular sleep stage, or is underdoing DEB.

Finally, at step 810 of method 800, a summary of the sleep session is generated. In some implementations, the summary is presented as a hypnogram, as illustrated in FIGS. 7A-7C. In other implementations, the summary comprises or consists of the data indicative of the time spent in each sleep stage over the course of the sleep session. In either implementations, the summary can include the number of distinct atypical REM sleep stages that the user experienced during the sleep session, and/or the total time spent in atypical REM sleep stages during the current sleep session. In some implementations, historical summaries of prior sleep sessions can be compared to the summary of the current sleep session. This comparison can be used to aid in confirming the number of atypical REM sleep stages experienced by the user during the sleep session, as well as the time spent in atypical REM sleep stages during the sleep session. These comparisons can also be used to monitor long-term trends of the user. For example, if a comparison of sleep sessions over a time period indicates that the user is experiencing increasingly more atypical REM sleep stages, the system 100 may notify the user or a third-party, and provide a recommendation.

Figure 9:
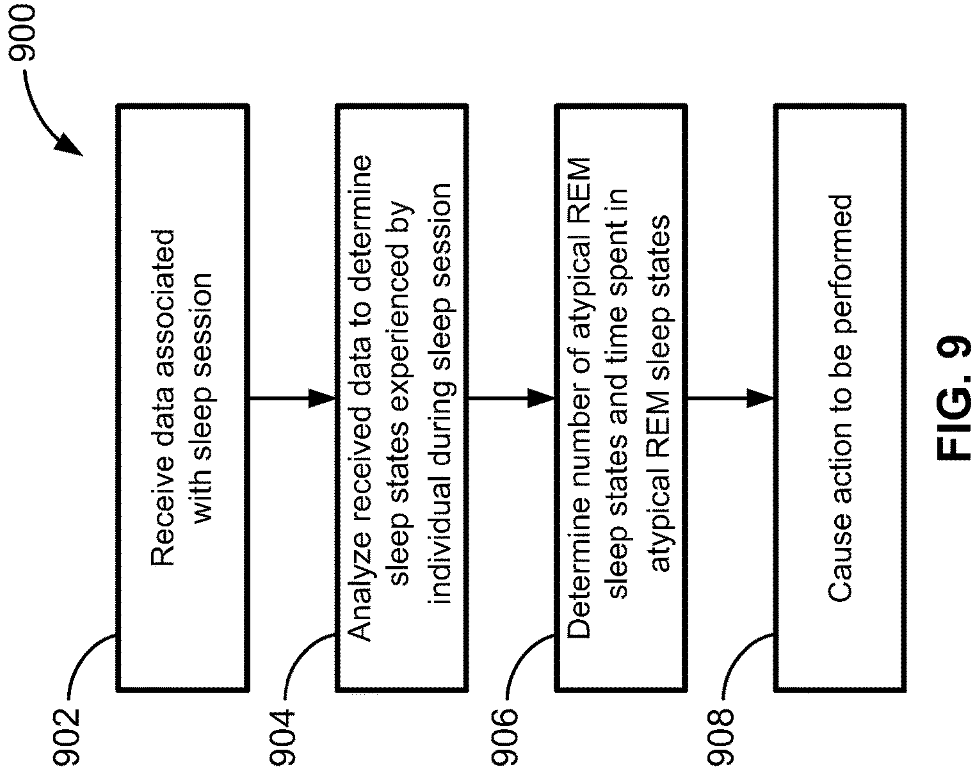
FIG. 9 is a process flow diagram for a second method of monitoring a sleep session, according to some implementations of the present disclosure.

Referring to FIG. 9, a method 900 for monitoring a sleep session is illustrated. Generally, a control system (such as the control system 110 of the system 100) or a portion of the control system such as a processor (such as the one or more processors 112) is configured to carry out the various steps of method 900 (or other methods disclosed herein). A memory device (such as the memory device 114 of the system 100) can be used to store any type of data utilized in the steps of method 900 (or other methods). Method 900 is a specific implementation of example algorithms 500 and 600, which can be used with a variety of different methods.

Step 902 of method 900 includes receiving data associated with a sleep session of the user, similar to step 802 of method 800. The received data can include a variety of different types of data, such as respiration data, motion data indicative of motion of the individual during the sleep session, audio data indicative of vocalizations detected during the sleep session, optical data indicative of light in an area where the individual is located during the sleep session, or any combination thereof. The data can also include temporal data indicative of a time elapsed during the sleep session. The data can be generated, for example, using any one or more of sensors 130.

Step 904 of method 900 includes analyzing the received data to identify the sleep stages experienced by the user during the sleep session. The sleep stages can include a light sleep stage, a deep sleep stage, a typical REM sleep stage, an atypical REM sleep stage, and a wake state. During the sleep session, the user will generally cycle through the various sleep stages in a periodic or semi-periodic fashion. Thus, in some implementations, the sleep session can be divided into a plurality of smaller sleep cycles, where each sleep cycle includes at least one light sleep stage, at least one deep sleep stage, and at least one REM sleep stage, which could be typical, atypical, or both. In some implementations, one or more trained algorithms are used to identify the sleep stages of the sleep session. Generally, any of the techniques described herein, including those described with respect to step 808 of method 800, can be used at step 904.

At step 906, the number of atypical REM sleep stages the user experienced during the sleep session is determined, as well as the total time spent in atypical REM sleep stages during the sleep session. At step 908, an action is caused to be performed based on these determinations. In some implementations, if the number of atypical REM sleep stages or the amount of time spent in an atypical REM sleep stage exceeds a respective threshold, the action is caused to be performed.

The action that is caused to be performed can generally be any action related to the occurrence of atypical REM sleep stages. In some implementations, the action includes causing a notification or message to be transmitted to the user or a third party. The notification can contain an indication that the number of atypical REM sleep stages or the time spent in atypical REM sleep stages exceeded their respective thresholds, a suggestion of a next steps for the user to take (such as being therapy or treatment, taking medicine, seeing a doctor, etc.), or any other suitable notification or message. The third party could be a healthcare provider of the user (such as a doctor or a nurse), a family member of the user, a friend of the user, a caretaker of the user, or any other suitable third-party. In further implementations, the action includes updating the user's medical record with information about the number of atypical REM sleep stages and the time spent in atypical REM sleep stages during the sleep session.

In some implementations, the trained algorithms used to identify sleep stages, and in particular identify atypical REM sleep stages, can be updated with user feedback. For example, if it is determined that the user experienced one or more atypical REM sleep stages during the sleep session, the user (or a third-party, such as the user's bed partner) can be prompted to confirm that the user did experience one or more atypical REM sleep stages during the sleep session. In response to the confirmation or lack of confirmation, the trained algorithms can be updated, so that they can more accurately identify atypical REM sleep stages during subsequent sleep sessions. Audio and/or video data can also be used to confirm whether the user experienced one or more atypical REM sleep stages during the sleep session. Audio data can indicate whether the user made any vocalizations or other sounds indicative of atypical REM sleep stages, and video data can indicate whether the user experienced any movements indicative of atypical REM sleep stages.

In some implementations, the time spent in atypical REM sleep stages during the current sleep session can be compared to time spent in atypical REM sleep stages during one or more prior sleep sessions. In one example, the average amount of time spent in atypical REM sleep stages per sleep session is determined, and then compared to the total time spent in atypical REM sleep stages during the current session. If the user spent more than the average time in atypical REM sleep stages during the current sleep stages, the action can be performed in step 908. In addition, the average amount of time spent in atypical REM sleep stages per session can be updated with the data from the current sleep session. The action in step 908 can also be caused to be performed if the updated average time spent in atypical REM sleep stages per sleep session satisfies a threshold amount of time.

In other implementations, similar methods for analyzing the number of atypical REM sleep stages experienced in the sleep session can be utilized. Thus, the average number of atypical REM sleep stages experienced per sleep session across one or more prior sleep sessions is determined, and then compared to the number of atypical REM sleep stages in the current sleep session. If the number of atypical REM sleep stages in the current sleep session is higher, the action can be caused to be performed. The average number of atypical REM sleep stages per sleep session can also be updated with the data from the current sleep session, and if the updated average is above the threshold, the action can be caused to be performed.

Thus, method 900 can be used to monitor the user over a longer time period to determine of the user is developing RBD, by looking at the number of, and time spent in, atypical REM sleep stages. If the user begins to experience more atypical REM sleep stages or begins to spend a longer amount of time in atypical REM sleep stages, certain actions can be undertaken, which can include notifying the user that they may be developing or have RBD, or providing relevant information to third parties.

Figure 10:
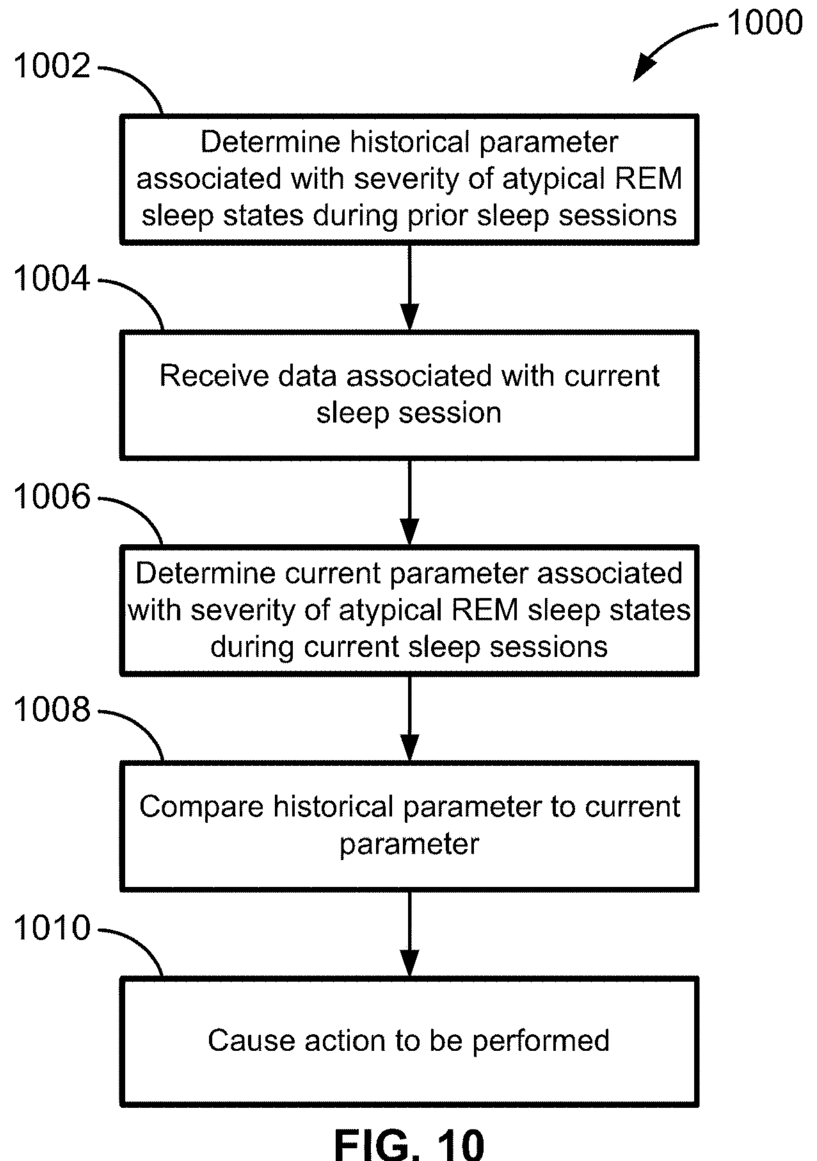
FIG. 10 is a process flow diagram for a third method of monitoring a sleep session, according to some implementations of the present disclosure.

Referring to FIG. 10, a method 1000 for monitoring a sleep session is illustrated. Generally, a control system (such as the control system 110 of the system 100) or a portion of the control system such as a processor (such as the one or more processors 112) is configured to carry out the various steps of method 1000 (or other methods disclosed herein). A memory device (such as the memory device 114 of the system 100) can be used to store any type of data utilized in the steps of method 1000 (or other methods). Method 1000 is a specific implementation of example algorithms 500 and 600, which can be used with a variety of different methods.

Step 1002 of method 1000 includes determining a historical parameter associated with a severity of atypical REM sleep stages experienced by the user in prior sleep sessions. Generally, the severity of atypical REM sleep stages can be quantified with reference to, for example, motion of the user during the atypical REM sleep stages or vocalizations made by the user during the atypical REM sleep stages. For example, atypical REM sleep stages characterized by violent and fast movements, or movements with large ranges of motion can be considered more severe. In contrast, atypical REM sleep stages characterized by slower and smaller movements (while still being the deliberate movements of RBD) can be considered to be less severe. In another example, atypical REM sleep stages characterized by louder vocalizations (speech or non-speech) can be considered more severe atypical REM sleep stages characterizes by quieter vocalizations (speech or non-speech). Monitoring the severity of atypical REM sleep stages (or of DEB experienced during the atypical REM sleep stages) can show the development of RBD in a user over a longer time period.

Step 1004 of method 1000 includes receiving data associated with a current sleep session. Step 1004 can be similar to step 802 of method 800 and step 902 of method 900. Step 1006 of method 1000 includes determining a current parameter associated with a severity of atypical REM sleep stages experienced during the current sleep session. Generally, the parameter associated with the severity of atypical REM sleep stages during the current sleep session is measured in the same manner as the historical parameter. In some implementations, the historical and current parameters can be measured on a scale from zero to ten.

Step 1008 of method 1000 includes comparing the current parameter to the historical parameter. Step 1010 of method 1000 includes causing an action to be performed based on this comparison. In some implementations, if the comparison indicates that the atypical REM sleep stages experienced during the current sleep session were more severe than the atypical REM sleep stages experienced during the one or more prior sleep sessions, the caused can be caused to be performed. The action of step 1010 can include notifying the user or a third-party that the atypical REM sleep stages are becoming more severe, which generally indicates that the user's RBD is progressing. The action could also include steps to reduce the user's movement or vocalizations during the atypical REM sleep stages. This action could be a real-time mitigation such as the DEB mitigation described in reference to at least step 806 of method 800. This action could also include suggesting to the user that they modify their sleep session to try and reduce the severity of the atypical REM sleep stages. This modification could be something as simple as reclining the bed slightly, or could be something more drastic such as partially restraining themselves during the sleep session.

In some implementations, the severity of any of the atypical REM sleep stages is based on motion of the user during the sleep sessions and/or vocalizations made by the user during the sleep sessions. In some implementations, the severity of atypical REM sleep stages is considered to have increased if the portion of the user that is moving (e.g., the user's arm) moves at a threshold speed, with a threshold acceleration, according to a predetermined movement pattern, for an amount of time greater than a predetermined threshold amount of time, or any combination thereof. Thus, atypical REM sleep stages become more severe if the user moves faster or with greater acceleration, begins to move with deliberate movement (as opposed to more random movements), or moves for a longer amount of time. Other motion characteristics can also be analyzed to determine if the atypical REM sleep stages are becoming more severe. Vocalizations made by the user can also be used to monitor the severity of the atypical REM sleep stages. For example, if the vocalizations made during the atypical REM sleep stages are louder than a threshold volume, have a certain pitch/frequency, or occur for a longer amount of time, the atypical REM sleep stages can be said to be becoming more severe.

Figure 11:
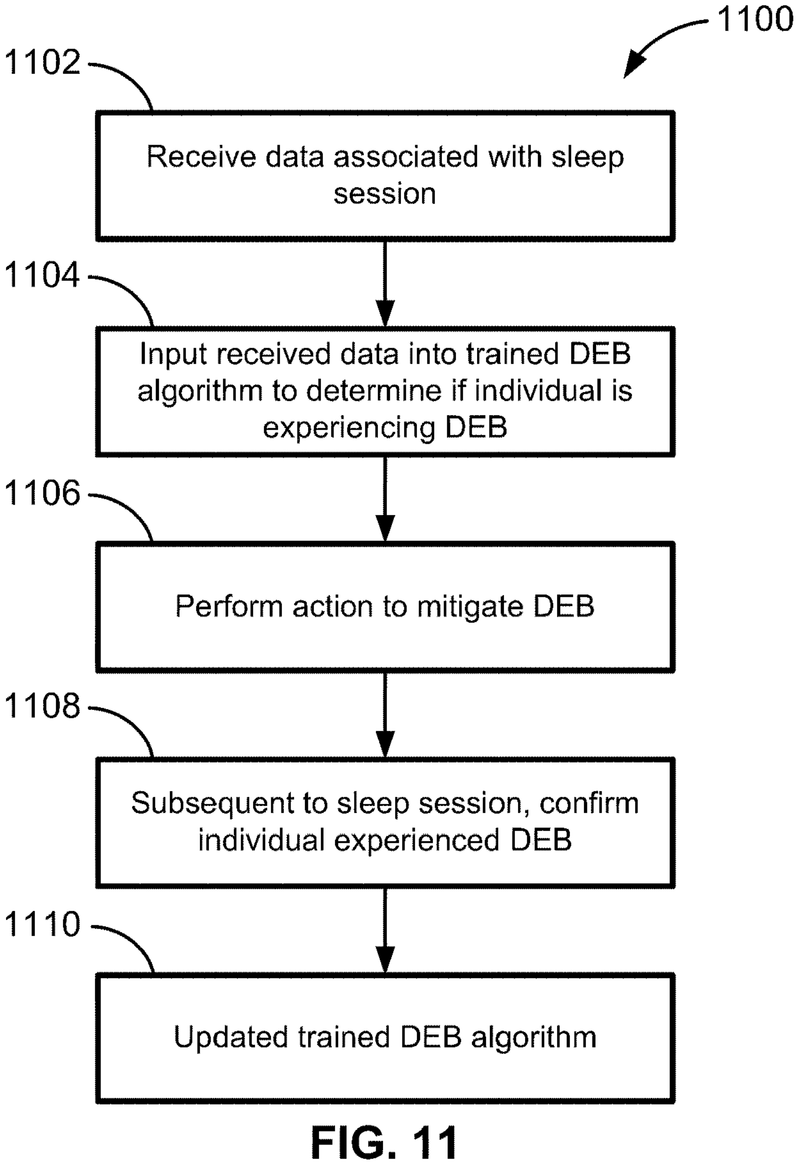
FIG. 11 is a process flow diagram for a fourth method of monitoring a sleep session, according to some implementations of the present disclosure.

Referring to FIG. 11, a method 1100 for monitoring a sleep session is illustrated. Generally, a control system (such as the control system 110 of the system 100) or a portion of the control system such as a processor (such as the one or more processors 112) is configured to carry out the various steps of method 1100 (or other methods disclosed herein). A memory device (such as the memory device 114 of the system 100) can be used to store any type of data utilized in the steps of method 1100 (or other methods). Method 1100 is a specific implementation of example algorithms 500 and 600, which can be used with a variety of different methods.

Step 1102 of method 1100 includes receiving data associated with a current sleep session. Step 1102 can be similar to step 802 of method 800, step 902 of method 900, and step 1004 of method 1000. Step 1104 of method 1100 includes inputting some or all of the received data into a trained DEB algorithm to determine if the individual is experiencing DEB during the sleep session. In some implementations, the DEB algorithm is trained using training data associated with prior sleep sessions where it is known that the user experienced DEB. Thus, motion data indicative of motion during DEB, respiration data indicative of respiration during DEB, and audio data indicative of vocalizations detected during DEB (or other sounds detected during prior sleep sessions) can all be used to train the DEB algorithm. The DEB algorithm can also be trained using audio data indicative of vocalizations (speech or non-speech) made by the user when the user is awake, or other data.

In some implementations, the DEB algorithm is additionally or alternatively trained using population-level training data. Generally, the user will be a member of a certain population of interest, which can be characterized by a variety of factors, including demographic factors such as age, sex, gender, underlying medical conditions, etc. Respiration, motion, and audio data associated with other members of the user's population can be used to train the DEB algorithm, and in particular data associated with known instances of DEB experienced by the members of the population.

In some implementations, the DEB algorithm is trained using neural networks. In some implementations, the DEB algorithm is trained by extracting features from various sleep metrics, such as respiration rate and movement level, and inputting those features into classifiers such as a support vector machine (SVM) regression.

Step 1106 of method 1100 includes, in response to determining that the user is experiencing DEB during the sleep session, performing an action to mitigate the DEB. Step 1106 is thus similar to step 806 of method 800. Step 1108 of method 1100 includes confirming with the user that the user did experience DEB during the sleep session. This confirmation can include simply asking the user whether they experienced DEB. The confirmation could also include showing the user video or audio of the sleep session, and having the user indicate that they experienced DEB upon hearing or seeing the same. Any vocalizations recorded during the sleep session can be played back to the user, who is then prompted to confirm whether the vocalizations were made by them or not. Step 1110 of method 1100 includes updating the trained DEB algorithm based on this confirmation, to improve the accuracy of the DEB algorithm. The DEB algorithm can then be updated based on the user's answer, which thus aids in improving the ability of the DEB algorithm to distinguish between vocalizations made by the user and other sounds. In some implementations, additional data can be used to aid the user in confirming that the user made the vocalizations and responding to the prompt. For example, video data of the user during the sleep session can be used to display a video to the user from points in time during the sleep session when the sound was detected. This allows the user to easily confirm whether the sound was a vocalization (speech or non-speech) made by the user.

In some implementations, the thresholds referred to herein (e.g., amount of movement, respiration rate, respiration rate variability, light level, elapsed time, number of atypical REM sleep stages, amount of time experiencing atypical REM sleep stages, etc.) can generally be determined by pre-training any of the algorithms or modules discussed herein, including algorithm 500, algorithm 600, the DEB algorithm, and the algorithm used to identify sleep stages. In some implementations, the algorithms and modules can be pre-trained using existing clinical data from patients known to exhibit RBD, and for which there is a suitable source of data available (such as polysomnography (PSG) data). These thresholds can be re-trained (e.g., updated) by using user-specific information. For example, if RBD is detected (e.g., by identifying DEB or atypical REM sleep stages) in previous sleep sessions recorded by the user, the various thresholds used for identifying DEB or atypical REM sleep stages can be adjusted. The thresholds can be adjusted based on user confirmation of DEB or atypical REM sleep stages, based on data confirming that the user specifically experienced DEB or atypical REM sleep stages (such as vocal data), or based on any other suitable mechanism.

The trained DEB algorithm can also be updated using one or more hypnograms that are generated from previous sleep sessions of the user. The hypnogram can indicate both the number of atypical REM sleep stages experienced by the user during the sleep session, as well as the total number of atypical REM sleep stages experienced by the user during the sleep session. Because the hypnogram does not need to be generated until the end of the sleep session, the hypnogram can generally utilize more data in identifying various different sleep stages the user was in during the sleep session. Thus, the hypnogram may include a more accurately backward-looking view of DEB experienced by the user during the sleep session, as compared to the real-time detection employed during the sleep session. Thus, the DEB algorithm can be updated using the hypnogram to improve the accuracy of the DEB algorithm. In some implementations, the DEB algorithm can originally be trained using hypnograms from the user or from other users.

In other implementations, the thresholds can also be determined based on user input. For example, the user could indicate to the system when the light level in the room is at the level it typically is during a sleep session, and when the user is awake before or after the sleep session. These light levels can then be used to determine the threshold light levels used for any methods or algorithms described herein. In still other implementations, the system could detect when the user is awake or asleep by some other method (user confirmation, data from sensors, etc.), and detect the values of various parameters to determine the thresholds for those parameters.

Generally, any of methods 800, 900, 1000, and 1100 can be implemented using a system having a control system with one or more processors, and a memory storing machine readable instructions. The controls system can be coupled to the memory, and methods 800-1100 can be implemented when the machine readable instructions are executed by at least one of the processors of the control system. Methods 800-1100 can also be implemented using a computer program product (such as a non-transitory computer readable medium) comprising instructions that when executed by a computer, cause the computer to carry out the steps of methods 800-1100.

One or more elements or aspects or steps, or any portion(s) thereof, from one or more of any of the claims below can be combined with one or more elements or aspects or steps, or any portion(s) thereof, from one or more of any of the other claims below, to form one or more additional implementations and/or claims of the present disclosure.

While the present disclosure has been described with reference to one or more particular embodiments or implementations, those skilled in the art will recognize that many changes may be made thereto without departing from the spirit and scope of the present disclosure. Each of these implementations and obvious variations thereof is contemplated as falling within the spirit and scope of the present disclosure. It is also contemplated that additional implementations according to aspects of the present disclosure may combine any number of features from any of the implementations described herein.

What is claimed is:

1. A method for monitoring a sleep session of an individual, the method comprising:

receiving data associated with a current sleep session of the individual, the data including temporal data associated with the current sleep session;

analyzing at least a portion of the received data to identify one or more sleep stages experienced by the individual during the current sleep session, the one or more sleep stages including a light sleep stage, a deep sleep stage, a typical rapid eye movement (REM) stage, an atypical REM stage, a wake stage, or any combination thereof, the analyzing including distinguishing between one or more atypical REM sleep stages and one or more wake stages based at least in part on the temporal data; and generating a summary of the current sleep session, the summary including (i) a number of the one or more atypical REM sleep stages experienced by the individual during the current sleep session, (ii) a time spent in atypical REM sleep stages during the current sleep session, or (iii) both (i) and (ii).

2. The method of claim 1, wherein the received data further includes (i) respiration data, (ii) motion data indicative of motion of the individual during the current sleep session, (iii) audio data indicative of sound detected during the current sleep session, (iv) optical data indicative of light in an area where the individual is located during the sleep session, or (v) any combination thereof.

3. The method of claim 2, wherein distinguishing between the one or more atypical REM sleep stages and the one or more wake stages includes:

tracking a time elapsed since a beginning of the current sleep session based at least in part on the temporal data;

analyzing the motion data to detect if the individual is currently moving;

in response to a first amount of time having elapsed since the beginning of the current sleep session and detecting the individual is currently moving, determining that the individual is currently in the wake stage; and/or in response to a second amount of time having elapsed since the beginning of the current sleep session and detecting the individual is currently moving, determining that the individual is currently in the atypical REM sleep stage, the second amount of time being greater than the first amount of time.

4. The method of claim 2, further comprising:

determining an amount of movement of the individual during the sleep session based on the motion data;

determining a respiration rate or a respiration rate variability of the individual during the sleep session based on the respiration data;

in response to determining that the amount of movement of the individual is less than a threshold amount of movement and that the respiration rate or the respiration rate variability of the individual is greater than a threshold respiration rate or a threshold respiration rate variability, determining that the individual is not in a typical REM sleep stage; and/or in response to determining that the amount of movement of the individual is greater than the threshold amount of movement and that the respiration rate or the respiration rate variability of the individual is greater than the threshold respiration rate or the threshold respiration rate variability, determining that the individual is in an atypical REM sleep stage.

5. The method of claim 2, wherein distinguishing between the one or more atypical REM sleep stages and the one or more wake stages includes:

determining an amount of movement of the individual during the sleep session based on the motion data;

determining a light level of the area where the individual is located during the sleep session based on the optical data;

in response to determining that the amount of movement of the individual is greater than a threshold amount of movement and that the light level of the area where the individual is located is greater than a threshold light level, determining that the individual is in a wake stage; and/or in response to determining that the amount of movement of the individual is greater than the threshold amount of movement and that the light level of the area where the individual is located is less than the threshold light level, determining that the individual is in an atypical REM sleep stage.

6. The method of claim 2, wherein distinguishing between the one or more atypical REM sleep stages and the one or more wake stages includes:

determining whether the sound detected during the current sleep session is speech made by the individual;

determining a light level of the area where the individual is located during the sleep session based on the optical data;

in response to determining that the detected sound is speech made by the individual and that the light level of the area where the individual is located is greater than a threshold light level, determining that the individual is in a wake stage; and/or in response to determining that the detected sound is speech made by the individual and that the light level of the area where the individual is located is less than the threshold light level, determining that the individual is in an atypical REM sleep stage.

7. The method of claim 2, wherein distinguishing between the one or more atypical REM sleep stages and the one or more wake stages includes:

determining whether the sound detected during the current sleep session is speech made by the individual;

determining a time elapsed during the current sleep session based at least in part on the temporal data;

in response to determining that the detected sound is speech made by the individual and that the time elapsed during the current sleep session is less than a threshold time, determining that the individual is in a wake stage; and/or in response to determining that the detected sound is speech made by the individual and that the time elapsed during the current sleep session is greater than the threshold time, determining that the individual is in an atypical REM sleep stage.

8. The method of claim 2, wherein distinguishing between the one or more atypical REM sleep stages and the one or more wake stages includes:

determining an amount of movement of the individual during the sleep session based on the motion data;

determining a time elapsed during the current sleep session based at least in part on the temporal data;

in response to determining that the amount of movement of the individual is greater than a threshold amount of movement and that the time elapsed during the current sleep session is less than a threshold time, determining that the individual is in a wake stage; and/or in response to determining that the amount of movement of the individual is greater than a threshold amount of movement and that the time elapsed during the current sleep session is greater than the threshold time, determining that the individual is in an atypical REM sleep stage.

9. The method of claim 2, further comprising (i) determining an amount of movement of the individual during the sleep session based on the motion data, the amount of movement of the individual being above a threshold amount of movement indicating that the individual is in an atypical REM sleep stage, (ii) determining whether the detected sound is speech made by the individual, the detected sound being speech by the individual indicating that the individual is in an atypical REM sleep stage, (iii) determining a light level of the area where the individual is located during the sleep session, the determined light level being greater than a threshold light level indicating that the individual is in a wake stage, or (iv) any combination of (i)-(iii).

10. The method of claim 1, further comprising:

determining a time elapsed during the current sleep session based at least in part on the temporal data; and based on one or more previous sleep stages already experienced by the individual during the sleep session and the time elapsed during the current sleep session, identifying a current sleep stage.

11. The method of claim 1, further comprising:

receiving historical data associated with one or more prior sleep sessions of the individual;

generating a historical summary of the one or more prior sleep sessions of the individual, the historical summary including a number of atypical REM sleep stages experienced by the individual during the one or more prior sleep sessions, and a time spent in atypical REM sleep stages during the one or more prior sleep sessions; and comparing the historical summary of the one or more prior sleep sessions to the summary of the current sleep session, to aid in confirming the number of atypical REM sleep stages experienced by the individual during the current sleep session, and the time spent in atypical REM sleep stages during the current sleep session.

12. The method of claim 1, further comprising:

analyzing, using a trained dream enactment behavior (DEB) algorithm, at least the portion of the received data to determine whether the individual is undergoing DEB during the current sleep session; and in response to a determination that the individual is undergoing DEB, causing an action to be performed, the action being configured to (i) aid in ending the DEB, (ii) aid in mitigating an impact of the DEB on the individual, (iii) aid in mitigating an impact of the DEB on a bed partner of the individual, or (iv) any combination thereof.

13. The method of claim 12, further comprising:

receiving historical data associated with one or more prior sleep sessions of the individual, the historical data including data related to confirmed instances of the individual undergoing DEB during at least one of the one or more prior sleep sessions; and comparing the historical data associated with one or more prior sleep sessions to the data associated with the current sleep session, to aid in determining whether the individual is undergoing DEB during the current sleep session.

14. The method of claim 12, wherein the action includes activating a light source, activating an audible alarm, causing a bed on which the individual is lying to move, or causing the individual to be physically moved.

15. The method of claim 1, further comprising causing an action to be performed in response to the summary indicating that (i) the number of atypical REM sleep stages experienced by the individual during the current sleep session satisfies a threshold number, (ii) a time spent in atypical REM sleep stages during the current sleep session is greater than a threshold time, or (iii) both (i) and (ii).

16. The method of claim 1, wherein the analyzing includes:

selecting one or more unidentified sleep stages by determining, based on non-temporal data, that each respective unidentified sleep stage is either a wake stage or an atypical REM sleep stage;

for each respective unidentified sleep stage, determining a time elapsed within the sleep session based on a portion of the temporal data associated with the respective unidentified sleep stage; and determining whether each respective unidentified sleep stage is a wake stage or an atypical REM sleep stage based on the time elapsed within the sleep session for the respective unidentified sleep stage.

17. The method of claim 1, wherein the data associated with the current sleep session of the individual further includes motion data, and wherein the analyzing includes:

determining that one or more unidentified sleep stages are either a wake stage or an atypical REM sleep stage by analyzing at least the motion data; and determining a time elapsed within the sleep session for each respective unidentified sleep stage based on a portion of the temporal data associated with the respective unidentified sleep stage to determine whether each respective unidentified sleep stage is a wake stage or an atypical REM sleep stage.

18. The method of claim 1, wherein the data associated with the current sleep session of the individual further includes audio data, and wherein the analyzing includes:

determining that one or more unidentified sleep stages are either a wake stage or an atypical REM sleep stage by analyzing at least the audio data; and determining a time elapsed within the sleep session for each respective unidentified sleep stage based on a portion of the temporal data associated with the respective unidentified sleep stage to determine whether each respective unidentified sleep stage is a wake stage or an atypical REM sleep stage.

19. A system comprising:

an electronic interface configured to receive data associated with a current sleep session of an individual, the data including temporal data associated with the current sleep session;

a memory storing machine-readable instructions; and a control system including one or more processors configured to execute the machine-readable instructions to:

analyze at least a portion of the received data to identify one or more sleep stages experienced by the individual during the current sleep session, the one or more sleep stages including a light sleep stage, a deep sleep stage, a typical rapid eye movement (REM) stage, an atypical REM stage, a wake stage, or any combination thereof, the analyzing including distinguishing between one or more atypical REM sleep stages and one or more wake stages based at least in part on the temporal data; and generate a summary of the current sleep session, the summary including (i) a number of the one or more atypical REM sleep stages experienced by the individual during the current sleep session, (ii) a time spent in atypical REM sleep stages during the current sleep session, or (iii) both (i) and (ii).

20. A method for monitoring a sleep session of an individual, the method comprising:

receiving data associated with a current sleep session of the individual, the data including at least temporal data associated with the current sleep session and motion data indicative of motion of the individual during the current sleep session;

analyzing at least a portion of the received data to identify one or more sleep stages experienced by the individual during the current sleep session, the one or more sleep stages including a light sleep stage, a deep sleep stage, a typical rapid eye movement (REM) stage, an atypical REM stage, a wake stage, or any combination thereof, the analyzing including:

tracking a time elapsed since a beginning of the current sleep session based at least in part on the temporal data;

analyzing the motion data to detect if the individual is currently moving;

in response to a first amount of time having elapsed since the beginning of the current sleep session and detecting the individual is currently moving, determining that the individual is currently in the wake stage; and/or in response to a second amount of time having elapsed since the beginning of the current sleep session and detecting the individual is currently moving, determining that the individual is currently in the atypical REM sleep stage, the second amount of time being greater than the first amount of time; and generating a summary of the current sleep session, the summary including (i) a number of atypical REM sleep stages experienced by the individual during the current sleep session, (ii) a time spent in atypical REM sleep stages during the current sleep session, or (iii) both (i) and (ii).

* * * * *